(12) United States Patent
McConnell et al.

(10) Patent No.: US 9,133,269 B2
(45) Date of Patent: Sep. 15, 2015

(54) HUMANIZED ANTIBODIES DIRECTED AGAINST COMPLEMENT PROTEIN C5

(71) Applicant: ANAPTYSBIO, INC., San Diego, CA (US)

(72) Inventors: Audrey McConnell, San Diego, CA (US); Peter M. Bowers, San Diego, CA (US); David J. King, Encinitas, CA (US)

(73) Assignee: AnaptysBio, Inc., San Diego, CA (US)

( * ) Notice: Subject to any disclaimer, the term of this patent is extended or adjusted under 35 U.S.C. 154(b) by 0 days.

(21) Appl. No.: 13/972,524

(22) Filed: Aug. 21, 2013

(65) Prior Publication Data

US 2014/0056878 A1   Feb. 27, 2014

Related U.S. Application Data

(60) Provisional application No. 61/692,765, filed on Aug. 24, 2012.

(51) Int. Cl.
*A61K 39/395* (2006.01)
*C07K 16/18* (2006.01)
*C07K 16/36* (2006.01)

(52) U.S. Cl.
CPC .............. *C07K 16/18* (2013.01); *C07K 2317/24* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS 7,432,356 B2   10/2008   Fung et al.
8,206,716 B2    6/2012   Fung et al.

OTHER PUBLICATIONS

Rudikoff et al., (Proc Natl Acad Sci USA 79: 1979-1983 (1982).*
Colman, Research in Immunology 145: 33-36 (1994).*
Kussie et al., J. Immunol. 152: 146-152 (1994).*
Chen et al., EMBO J., 14: 2784-2794 (1995).*
Almagro, *Front Biosci* 13, 1619-1633 (2008).
Bowers et al., *Proc. Natl. Acad. Sci. USA*, 108: 20455-20460 (2011).
Bramham et al., *J. Biol. Chemistry*, 280: 10636-10645 (2005).
Carter, *Nature Reviews Immunol* 6, 343-357 (2006).
Copland et al., *Clinical and Experimental Immunol.*, 159: 303-314 (2010).
Dmytrijuk et al., *The Oncologist*, 13(9): 993-1000 (2008).
Gilles et al., *BMC Genomics* 12, 245 (2011).
Glanville et al., *Proc. Natl. Acad. Sci. USA* 106, 20216-20221 (2009).
Goldstein et al., *New Engl. J. Med.* 313, 337-342 (1985).
Ho et al., *Gene* 77, 51-59 (1989).
Hoet et al., *Nature Biotechnology* 23, 344-348 (2005).
Hoogenboom, *Nature Biotechnology* 23, 1105-1116 (2005).
Kaplan, *Curr. Opin. Investig. Drugs*, 3: 1017-1023 (2002).
Kasper et al., *Current Medical Research and Opinion* 22, 1671-1678 (2006).
Knappik et al., *Journal of Molecular Biology* 296, 57-86 (2000).
Koboldt et al., *Bioinformatics* (Oxford, England) 25, 2283-2285 (2009).
Kohler, *Nature* 256, 495-497 (1975).
Lonberg, *Nature Biotechnology* 23, 1117-1125 (2005).
Mahaffey et al., *Circulation*, 108: 1176-1183 (2003).
Martin et al., *Am J Reprod Immunol* 58, 138-149 (2007).
Muller-Eberhard, *Annual Review of Immunology* 4, 503-528 (1986).
Padlan, *Molecular Immunology* 31, 169-217 (1994).
Peitsch et al., *Curr. Opin. Cell. Biol.*, 3(4): 710-716 (1991).
Persic et al., *Gene* 187, 1-8 (1997).
Rother et al., *Nat. Biotechnology*, 25: 1256-1264 (2007).
Schatz et al., *Annual Review of Immunology* 10, 359-383 (1992).
Schwarz et al., *Arthritis Research & Therapy* 9 (Suppl 1), S7 (2007).
Tack et al., *Biochemistry*, 18(8): 1490-1497 (1979).
Teeling et al., *Blood* 104, 1793-1800 (2004).
Thomas et al., *Mol. Immunol.*, 33: 1389-1401 (1996).
Trendelenburg, *Swiss Med. Wkly.*, 137: 413-417 (2007).
Vendel et al., *Archives of Biochemistry and Biophysics*, 526:2, 188-193 (2012).
Wang et al., *Nat. Med.*, 17(2): 1674-1679 (2011).
Whiss, *Curr. Opin. Investig. Drugs*, 3: 870-877 (2002).
Kunik et al., "Paratome: an online tool for systematic identification of antigen-binding regions in antibodies based on sequence or structure," *Nucleic Acids Research*, 1-4 (2012).

* cited by examiner

*Primary Examiner* — Phillip Gambel
(74) *Attorney, Agent, or Firm* — Leydig, Voit & Mayer, Ltd.

(57) ABSTRACT

The invention relates to an isolated immunoglobulin heavy chain polypeptide and an isolated immunoglobulin light chain polypeptide that binds to complement protein C5. The invention provides a C5-binding agent that comprises the aforementioned immunoglobulin heavy chain polypeptide and immunoglobulin light chain polypeptide. The invention provides an isolated complement protein C5 epitope. The invention also provides related vectors, compositions, and methods of using the C5-binding agent to treat an C5-mediated disease.

34 Claims, 3 Drawing Sheets

SEQUENCE LISTING

```
<160> NUMBER OF SEQ ID NOS: 29

<210> SEQ ID NO 1
<211> LENGTH: 119
<212> TYPE: PRT
<213> ORGANISM: Artificial Sequence
<220> FEATURE:
<223> OTHER INFORMATION: Synthetic sequence

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Arg Tyr Asn Tyr Phe Asp Tyr Trp Gly Gln Gly
            100                 105                 110

Thr Thr Leu Thr Val Ser Ser
        115

<210> SEQ ID NO 2
<211> LENGTH: 119
<212> TYPE: PRT
<213> ORGANISM: Artificial Sequence
<220> FEATURE:
<223> OTHER INFORMATION: Synthetic sequence

<400> SEQUENCE: 2
```

```
Glu Val Gln Leu Leu Glu Ser Gly Gly Gly Leu Val Gln Pro Gly Gly
1               5                   10                  15

Ser Pro Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Leu Arg Tyr Asn Tyr Phe Asp Tyr Trp Gly Gln Gly
            100                 105                 110

Thr Thr Leu Thr Val Ser Ser
            115
```

```
<210> SEQ ID NO 3
<211> LENGTH: 118
<212> TYPE: PRT
<213> ORGANISM: Artificial sequence
<220> FEATURE:
<223> OTHER INFORMATION: Synthetic sequence

<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Gly Leu Arg Tyr Asn Tyr Phe Asp Tyr Trp Gly Gln Gly Thr
            100                 105                 110

Thr Leu Thr Val Ser Ser
        115
```

```
<210> SEQ ID NO 4
<211> LENGTH: 119
<212> TYPE: PRT
<213> ORGANISM: Artificial sequence
<220> FEATURE:
<223> OTHER INFORMATION: Synthetic sequence

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Ser Thr Tyr Tyr Ala Asp Ser Val
```

```
                   50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Leu Arg Tyr Asn Tyr Phe Asp Tyr Trp Gly Gln Gly
                100                 105                 110

Thr Thr Leu Thr Val Ser Ser
            115

<210> SEQ ID NO 5
<211> LENGTH: 119
<212> TYPE: PRT
<213> ORGANISM: Artificial sequence
<220> FEATURE:
<223> OTHER INFORMATION: Synthetic sequence

<400> SEQUENCE: 5

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Gly Leu Arg Tyr Lys Tyr Phe Asp Tyr Trp Gly Gln Gly
                100                 105                 110

Thr Thr Leu Thr Val Ser Ser
            115

<210> SEQ ID NO 6
<211> LENGTH: 110
<212> TYPE: PRT
<213> ORGANISM: Artificial sequence
<220> FEATURE:
<223> OTHER INFORMATION: Synthetic sequence

<400> SEQUENCE: 6

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Glu Tyr Thr Phe Gly Gln Gly Thr Lys Leu Glu Ile Lys Arg
                100                 105                 110
```

<210> SEQ ID NO 7
<211> LENGTH: 110
<212> TYPE: PRT
<213> ORGANISM: Artificial sequence
<220> FEATURE:
<223> OTHER INFORMATION: Synthetic sequence

<400> SEQUENCE: 7

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ile Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Glu Tyr Thr Phe Gly Gln Gly Thr Lys Leu Glu Ile Lys Arg
            100                 105                 110
```

<210> SEQ ID NO 8
<211> LENGTH: 110
<212> TYPE: PRT
<213> ORGANISM: Artificial sequence
<220> FEATURE:
<223> OTHER INFORMATION: Synthetic sequence

<400> SEQUENCE: 8

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Glu Tyr Thr Phe Gly Gln Gly Thr Lys Leu Glu Ile Lys Arg
            100                 105                 110
```

<210> SEQ ID NO 9
<211> LENGTH: 110
<212> TYPE: PRT
<213> ORGANISM: Artificial sequence
<220> FEATURE:
<223> OTHER INFORMATION: Synthetic sequence

<400> SEQUENCE: 9

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
```

```
            35                  40                  45
Ile Tyr Gly Ala Ser Ser Arg Ala Thr Gly Ile Pro Asp Arg Phe Ser
         50                  55                  60
Gly Ser Gly Ser Val Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
Glu Tyr Thr Phe Gly Gln Gly Thr Lys Leu Glu Ile Lys Arg
            100                 105                 110

<210> SEQ ID NO 10
<211> LENGTH: 110
<212> TYPE: PRT
<213> ORGANISM: Artificial sequence
<220> FEATURE:
<223> OTHER INFORMATION: Synthetic sequence

<400> SEQUENCE: 10

Glu Ile Val Leu Thr Gln Ser Pro Gly Thr Leu Ser Leu Ser Pro Gly
  1               5                  10                  15
Glu Arg Ala Thr Leu Ser Cys Arg Ala Ser Gln Ser Val Ser Ser Ser
             20                  25                  30
Tyr Leu Ala Trp Tyr Gln Gln Lys Pro Gly Gln Ala Pro Arg Leu Leu
             35                  40                  45
Ile Tyr Gly Ala Ser Ser Arg Ala Thr Gly Ile Pro Asp Arg Phe Ser
         50                  55                  60
Gly Ser Gly Ser Glu Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
Glu Tyr Thr Phe Gly Gln Gly Thr Lys Leu Glu Ile Lys Arg
            100                 105                 110

<210> SEQ ID NO 11
<211> LENGTH: 110
<212> TYPE: PRT
<213> ORGANISM: Artificial sequence
<220> FEATURE:
<223> OTHER INFORMATION: Synthetic sequence

<400> SEQUENCE: 11

Glu Ile Val Leu Thr Gln Ser Pro Gly Thr Leu Ser Leu Ser Pro Gly
  1               5                  10                  15
Glu Arg Ala Thr Leu Ser Cys Arg Ala Ser Gln Ser Val Ser Ser Ser
             20                  25                  30
Tyr Leu Ala Trp Tyr Gln Gln Lys Pro Gly Gln Ala Pro Arg Leu Leu
             35                  40                  45
Ile Tyr Gly Ala Ser Ser Arg Ala Thr Gly Ile Pro Asp Arg Phe Ser
         50                  55                  60
Gly Ser Gly Ser Arg Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
Glu Tyr Thr Phe Gly Gln Gly Thr Lys Leu Glu Ile Lys Arg
            100                 105                 110

<210> SEQ ID NO 12
<211> LENGTH: 110
```

```
<212> TYPE: PRT
<213> ORGANISM: Artificial sequence
<220> FEATURE:
<223> OTHER INFORMATION: Synthetic sequence

<400> SEQUENCE: 12

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Arg Glu
65                  70                  75                  80

Pro Glu Asp Phe Ala Val Tyr Tyr Cys Gln Gln Tyr Gly Ser Ser Pro
                85                  90                  95

Glu Tyr Thr Phe Gly Gln Gly Thr Lys Leu Glu Ile Lys Arg
            100                 105                 110

<210> SEQ ID NO 13
<211> LENGTH: 110
<212> TYPE: PRT
<213> ORGANISM: Artificial sequence
<220> FEATURE:
<223> OTHER INFORMATION: Synthetic sequence

<400> SEQUENCE: 13

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Ala Glu Asp Phe Ala Val Tyr Tyr Cys Gln Gln Tyr Gly Ser Ser Pro
                85                  90                  95

Glu Tyr Thr Phe Gly Gln Gly Thr Lys Leu Glu Ile Lys Arg
            100                 105                 110

<210> SEQ ID NO 14
<211> LENGTH: 110
<212> TYPE: PRT
<213> ORGANISM: Artificial sequence
<220> FEATURE:
<223> OTHER INFORMATION: Synthetic sequence

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
```

```
            50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Asp Ser Ser Pro
                 85                  90                  95

Glu Tyr Thr Phe Gly Gln Gly Thr Lys Leu Glu Ile Lys Arg
                100                 105                 110
```

<210> SEQ ID NO 15
<211> LENGTH: 110
<212> TYPE: PRT
<213> ORGANISM: Artificial sequence
<220> FEATURE:
<223> OTHER INFORMATION: Synthetic sequence

<400> SEQUENCE: 15

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Arg Ser Leu
                 85                  90                  95

Glu Tyr Thr Phe Gly Gln Gly Thr Lys Leu Glu Ile Lys Arg
                100                 105                 110
```

<210> SEQ ID NO 16
<211> LENGTH: 110
<212> TYPE: PRT
<213> ORGANISM: Artificial sequence
<220> FEATURE:
<223> OTHER INFORMATION: Synthetic sequence

<400> SEQUENCE: 16

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Gly Ser Pro
                 85                  90                  95

Glu Tyr Thr Phe Gly Gln Gly Thr Lys Leu Glu Ile Lys Arg
                100                 105                 110
```

<210> SEQ ID NO 17
<211> LENGTH: 110
<212> TYPE: PRT
<213> ORGANISM: Artificial sequence
<220> FEATURE:

<223> OTHER INFORMATION: Synthetic sequence

<400> SEQUENCE: 17

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ile Ser Pro
                85                  90                  95

Glu Tyr Thr Phe Gly Gln Gly Thr Lys Leu Glu Ile Lys Arg
            100                 105                 110

<210> SEQ ID NO 18
<211> LENGTH: 110
<212> TYPE: PRT
<213> ORGANISM: Artificial sequence
<220> FEATURE:
<223> OTHER INFORMATION: Synthetic sequence

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Glu Tyr Thr Phe Gly Gln Gly Thr Lys Leu Glu Ile Lys Arg
            100                 105                 110

<210> SEQ ID NO 19
<211> LENGTH: 115
<212> TYPE: PRT
<213> ORGANISM: Artificial sequence
<220> FEATURE:
<223> OTHER INFORMATION: Synthetic sequence

<400> SEQUENCE: 19

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu

```
                65                  70                  75                  80
Pro Glu Asp Phe Ala Val Tyr Tyr Cys Gln Gln Tyr Gly Ser Ser Gln
                    85                  90                  95

Tyr Gly Ser Ser Pro Glu Tyr Thr Phe Gly Gln Gly Thr Lys Leu Glu
                100                 105                 110

Ile Lys Arg
        115

<210> SEQ ID NO 20
<211> LENGTH: 110
<212> TYPE: PRT
<213> ORGANISM: Artificial sequence
<220> FEATURE:
<223> OTHER INFORMATION: Synthetic sequence

<400> SEQUENCE: 20

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Ala
                85                  90                  95

Glu Tyr Thr Phe Gly Gln Gly Thr Lys Leu Glu Ile Lys Arg
                100                 105                 110

<210> SEQ ID NO 21
<211> LENGTH: 110
<212> TYPE: PRT
<213> ORGANISM: Artificial sequence
<220> FEATURE:
<223> OTHER INFORMATION: Synthetic sequence

<400> SEQUENCE: 21

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Thr
                85                  90                  95

Glu Tyr Thr Phe Gly Gln Gly Thr Lys Leu Glu Ile Lys Arg
                100                 105                 110

<210> SEQ ID NO 22
<211> LENGTH: 108
<212> TYPE: PRT
<213> ORGANISM: Artificial sequence
<220> FEATURE:
```

<223> OTHER INFORMATION: Synthetic sequence

<400> SEQUENCE: 22

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Thr Phe Gly Gln Gly Thr Lys Leu Glu Ile Lys Arg
            100                 105

<210> SEQ ID NO 23
<211> LENGTH: 110
<212> TYPE: PRT
<213> ORGANISM: Artificial sequence
<220> FEATURE:
<223> OTHER INFORMATION: Synthetic sequence

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Asp Tyr Thr Phe Gly Gln Gly Thr Lys Leu Glu Ile Lys Arg
            100                 105                 110

<210> SEQ ID NO 24
<211> LENGTH: 116
<212> TYPE: PRT
<213> ORGANISM: Artificial sequence
<220> FEATURE:
<223> OTHER INFORMATION: Synthetic sequence

<400> SEQUENCE: 24

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu

```
                65                  70                  75                  80
Pro Glu Asp Phe Ala Val Tyr Tyr Cys Gln Gln Tyr Gly Ser Ser Pro
                    85                  90                  95

Glu Tyr Gly Gly Ser Pro Glu Tyr Thr Phe Gly Gln Gly Thr Lys Leu
            100                 105                 110

Glu Ile Lys Arg
        115
```

<210> SEQ ID NO 25
<211> LENGTH: 5
<212> TYPE: PRT
<213> ORGANISM: Artificial sequence
<220> FEATURE:
<223> OTHER INFORMATION: Synthetic sequence

<400> SEQUENCE: 25

```
Gln Tyr Gly Ser Ser
1               5
```

<210> SEQ ID NO 26
<211> LENGTH: 6
<212> TYPE: PRT
<213> ORGANISM: Artificial sequence
<220> FEATURE:
<223> OTHER INFORMATION: Synthetic sequence

<400> SEQUENCE: 26

```
Gly Gly Ser Pro Glu Tyr
1               5
```

<210> SEQ ID NO 27
<211> LENGTH: 118
<212> TYPE: PRT
<213> ORGANISM: Artificial sequence
<220> FEATURE:
<223> OTHER INFORMATION: Synthetic sequence

<400> SEQUENCE: 27

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Thr Trp Val Arg Gln Ala Pro Gly Lys Gly Leu Glu Trp Val
        35                  40                  45

Ser Val Ile Ser Gly Ser Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Arg Gly Leu Arg Tyr Asn Tyr Phe Asp Tyr Trp Gly Gln Gly Thr
            100                 105                 110

Thr Leu Thr Val Ser Ser
        115
```

<210> SEQ ID NO 28
<211> LENGTH: 147
<212> TYPE: PRT
<213> ORGANISM: Artificial sequence
<220> FEATURE:
<223> OTHER INFORMATION: Synthetic sequence

```
<400> SEQUENCE: 28

Ala Asp Cys Gly Gln Met Gln Glu Leu Asp Leu Thr Ile Ser Ala
1               5                   10                  15

Glu Thr Arg Lys Gln Thr Ala Cys Lys Pro Glu Ile Ala Tyr Ala Tyr
            20                  25                  30

Lys Val Ser Ile Thr Ser Ile Thr Val Glu Asn Val Phe Val Lys Tyr
            35                  40                  45

Lys Ala Thr Leu Leu Asp Ile Tyr Lys Thr Gly Glu Ala Val Ala Glu
50                      55                  60

Lys Asp Ser Glu Ile Thr Phe Ile Lys Val Thr Cys Thr Asn Ala
65                  70                  75                  80

Glu Leu Val Lys Gly Arg Gln Tyr Leu Ile Met Gly Lys Glu Ala Leu
            85                  90                  95

Gln Ile Lys Tyr Asn Phe Ser Phe Arg Tyr Ile Tyr Pro Leu Asp Ser
                100                 105                 110

Leu Thr Trp Ile Glu Tyr Trp Pro Arg Asp Thr Thr Cys Ser Ser Cys
            115                 120                 125

Gln Ala Phe Leu Ala Asn Leu Asp Glu Phe Ala Glu Asp Ile Phe Leu
    130                 135                 140

Asn Gly Cys
145

<210> SEQ ID NO 29
<211> LENGTH: 481
<212> TYPE: DNA
<213> ORGANISM: Artificial sequence
<220> FEATURE:
<223> OTHER INFORMATION: Synthetic sequence

<400> SEQUENCE: 29
gctgattgtg ggcaaatgca ggaagaattg gatctgacaa tctctgcaga gacaagaaaa      60
caaacagcat gtaaaccaga gattgcgtat gcttataaag ttagcatcac atccatcact    120
gtagaaaatg tttttgtcaa gtacaaggca acccttctgg atatctacaa aactggggaa    180
gctgttgctg agaaagactc tgagattacc ttcattaaaa aggtaacctg tactaacgct    240
gagctggtaa aaggaagaca gtacttaatt atgggtaaag aagccctcca gataaaatac    300
aatttcagtt tcaggtacat ctacccttta gattccttga cctggattga atactggcct    360
agagacacaa catgttcatc gtgtcaagca tttttagcta atttagatga atttgccgaa    420
gatatctttt taaatggatg ctaaaattcc tgaagttcag ctgcatacag tttgcactta    480
t                                                                    481
```

US 9,133,269 B2

HUMANIZED ANTIBODIES DIRECTED AGAINST COMPLEMENT PROTEIN C5

Figure 1:
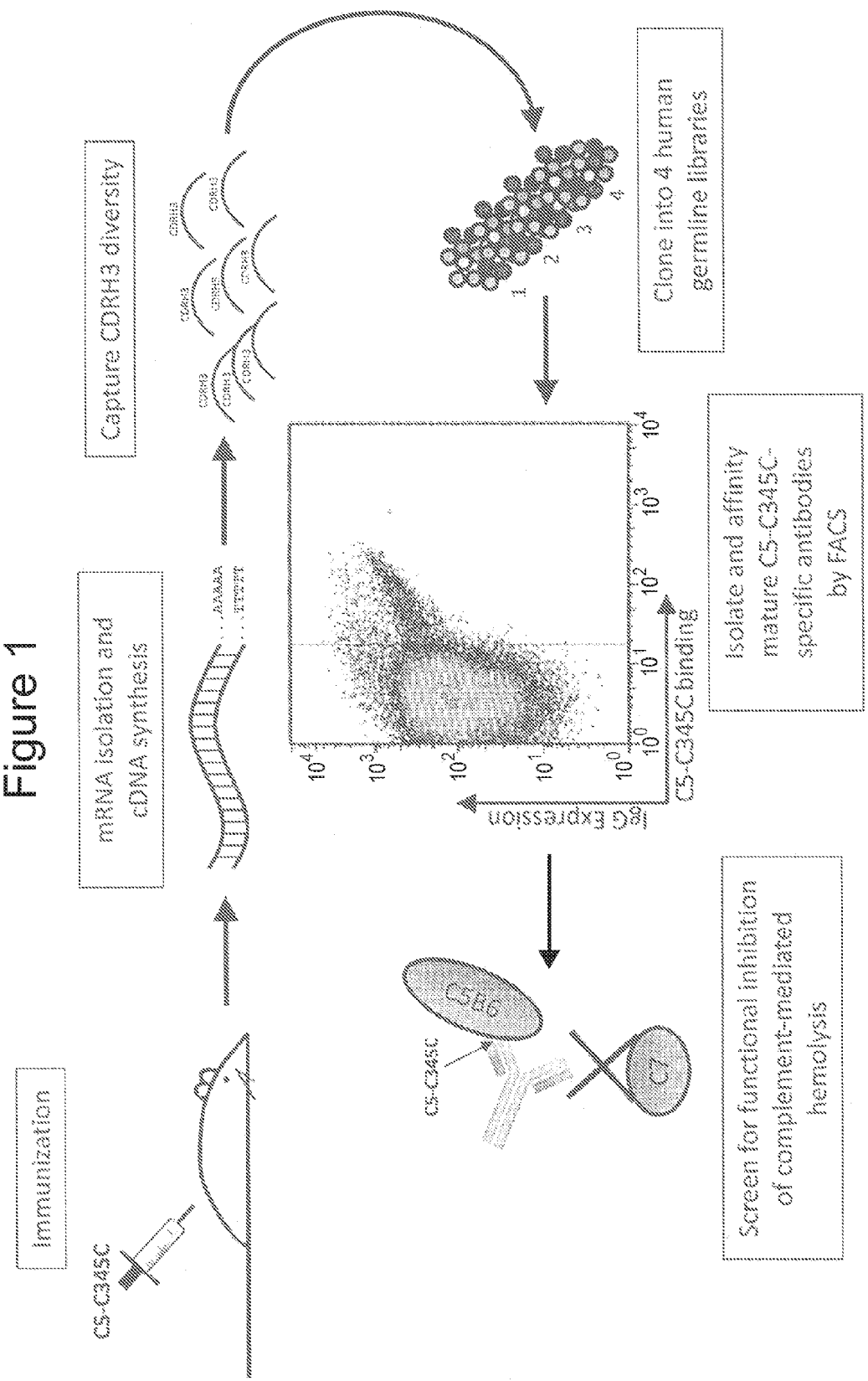

Incorporated by reference in its entirety herein is a computer-readable nucleotide/amino acid sequence listing submitted concurrently herewith and identified as follows: One 29,506 Byte ASCII (Text) file named "714139_SequenceListing_ST25.TXT," created on Aug. 21, 2013.

BACKGROUND OF THE INVENTION

The complement system is part of the innate immune system and includes a set of plasma proteins that act together to attack extracellular forms of pathogens. Activation of the complement system can occur in response to pathogens themselves or to antibodies bound to a pathogen. Upon activation, proteases in the complement system cleave specific proteins to release cytokines and initiate an amplifying cascade of further cleavage reactions. This activation cascade results in massive amplification of the responsee, with cleavage of C3 and C5 by their respective convertases as the terminal activation event. Cleavage of C5 results in formation of two distinct molecules: C5a and C5b. C5b reacts with complement proteins C6, C7, C8 and C9 to effect activation of the cell-killing membrane attack complex (MAC). The membrane attack complex forms transmembrane channels on the surface of pathogen cells, leading to cell lysis and death (Peitsch et al., Curr. Opin. Cell. Biol., 3(4): 710-716 (1991), and C. A. Janeway et al. (eds.), Immunobiology, 5th Ed., Garland Publishing, New York, N.Y. (2001)).

The complement system includes more than 30 proteins and protein fragments, including serum proteins, serosal proteins, and cell membrane receptors. Complement protein 5 (C5) is the fifth component of the complement system, and plays an important role in inflammatory and cell killing processes. The C5 protein is composed of alpha and beta polypeptide chains that are linked by a disulfide bridge. An activation peptide, C5a, which is an anaphylatoxin that possesses potent spasmogenic and chemotactic activity, is derived from the alpha polypeptide via cleavage with a convertase. C5a is short-lived in situ, and in the absence of binding to its cognate receptor, C5a is quickly degraded. Binding of C5a to the C5a receptor (C5aR) initiates a potent local inflammatory and immune response, and this pathway has been targeted for multiple disease indications such as myocardial infarction (MI) and graft-versus-host disease. Strategies for targeting the activity of C5a have included the inhibition of C5 cleavage and soluble C5aR-Fc constructs that compete for C5a binding with the endogenous receptor.

Following cleavage, complement protein C5b initiates formation of the membrane attack complex (MAC) in conjunction with proteins C6 and C7. The assembly process is mediated by the C5 C-terminal interaction domain C345C, which is 800 amino acids distal to the site of proteolytic activation. This site is thought to be critical for binding during MAC initiation because binding of C7 to this domain is essential for nonreversible MAC formation (see, e.g., Tack et al., Biochemistry, 18(8): 1490-1497 (1979); and Muller-Eberhard, H. J., Annual Review of Immunology, 4: 503-528 (1986)).

Inappropriate complement activation and MAC formation has been associated with a number of disease states, including, for example, paroxysmal nocturnal hemoglobinuria (PNH), uveoretinitis, atypical hemolytic uremic syndrome (aHUS), and osteoarthritis (see, e.g., Copland et al., Clinical and Experimental Immunol., 159: 303-314 (2010); Rother et al., Nat. Biotechnol., 25: 1256-1264 (2007); and Wang et al., Nat. Med., 17: 1674-1679 (2011)). Deficiencies in the gene encoding the complement protein C5 lead to complement component C5 deficiency, and also have been linked to increased susceptibility to liver fibrosis and rheumatoid arthritis (see, e.g., Tack et al., supra)

Eculizumab (SOLIRIS™) is a monoclonal antibody directed against the C5 complement protein, and currently is the only pharmaceutical that blocks C5 proteolysis activation, inhibiting formation of both C5a and C5b. Eculizumab is approved for clinical use to treat PNH and aHUS, but is associated with significant immune-suppressive side effects, including an increased risk of meningococcal infections (see, e.g., Dmytrijuk et al., The Oncologist, 13(9): 993-1000 (2008)).

Therefore, there is a need for a C5-binding agent (e.g., an antibody) that binds C5 complement protein with a high affinity, and effectively neutralizes C5b activity and subsequent C5b-dependent MAC formation in vivo, but that does not block C5a activation, thereby avoiding immune-suppressive effects. The invention provides such C5 complement protein-binding agents.

BRIEF SUMMARY OF THE INVENTION

The invention provides an isolated immunoglobulin heavy chain polypeptide comprising SEQ ID NO: 1, except that (a) one or more of residues 18, 35, 50, and 104 of SEQ ID NO: 1 are replaced with a different residue, and/or (b) residue 56 of SEQ ID NO: 1 is deleted.

The invention provides an isolated immunoglobulin heavy chain polypeptide which comprises an amino acid sequence that is at least 90% identical to any one of SEQ ID NOs: 2-5.

The invention provides an isolated immunoglobulin light chain polypeptide comprising SEQ ID NO: 6, except that (a) one or more of residues 31, 54, 69, 79, 81, 93, 94, 96, and 97 of SEQ ID NO: 6 are replaced with a different residue, (b) an amino acid sequence comprising QYGSS (SEQ ID NO: 25) is inserted into SEQ ID NO: 6 after residue 95, (c) an amino acid sequence comprising GGSPEY (SEQ ID NO: 26) is inserted into SEQ ID NO: 6 after residue 98, (d) residue 97 of SEQ ID NO: 6 is deleted, (e) residue 98 of SEQ ID NO: 6 is deleted, or (f) any combination of (a)-(e).

The invention provides an isolated immunoglobulin light chain polypeptide which comprises an amino acid sequence that is at least 90% identical to any one of SEQ ID NOs: 7-24.

The invention also provides an isolated or purified epitope of complement protein C5, which comprises the amino acid sequence of SEQ ID NO: 28.

BRIEF DESCRIPTION OF THE SEVERAL VIEWS OF THE DRAWING(S)

FIG. 1 is a schematic which depicts the isolation of high-affinity monoclonal antibodies from mice immunized against the C345C domain of complement C5 protein.

Figure 2:
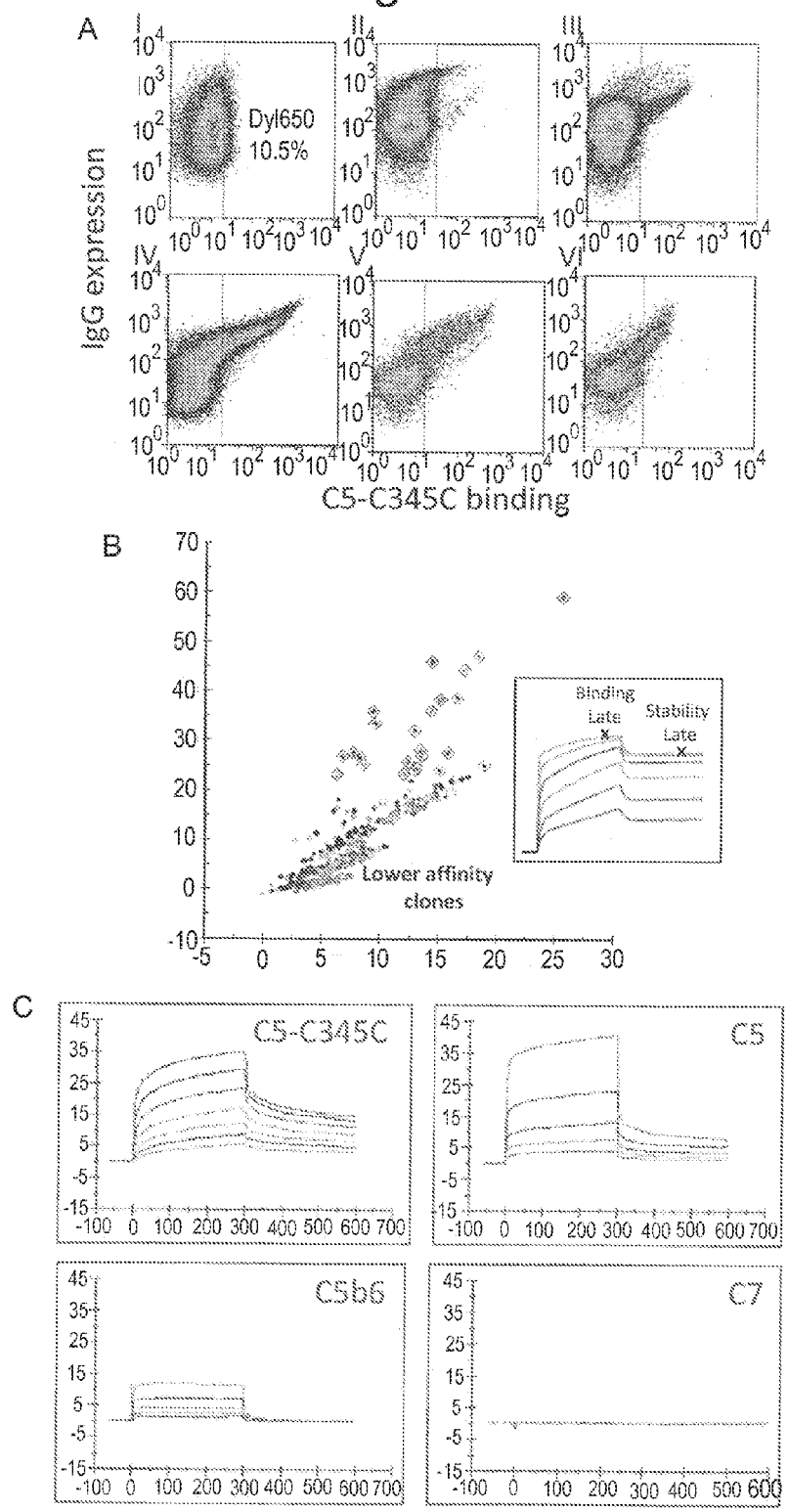

FIG. 2A are graphs which depict experimental data illustrating FACS results from isolation of a C5-C345C-specific antibody population from the sub-library pool containing IGHV3-30-3 and IGHV4-34 (panels I-III), and subsequent affinity maturation in strategy B (panels IV-VI). Approximately $5 \times 10^7$ cells were sorted per round. IgG expression is shown on the y-axis, and C5-C345C binding is shown on the x-axis.

FIG. 2B is a graph which depicts experimental data comparing stability late (value corresponds to amount of antibody-bound antigen) versus binding late (value corresponds to off-rate, $k_d$) capture-adjusted report points for a BIA- CORE™ 4000 screen of single cell clone supernatants as described in Example 1. Higher values correspond to more antigen bound per unit antibody (binding late) and slower off-rates (stability late).

FIG. 2C are graphs which depict experimental data illustrating a full kinetic analysis of APE777 binding to C5-C345C (first panel) with a $K_D$ of 200 nM ($k_a$=1.4×10$^5$ M$^{-1}$ s$^{-1}$, $k_d$=2.4×10$^{-2}$ s$^{-1}$). Binding of APE777 to C5 and C5b6 complement proteins was detectible (second and third panels), while APE777 showed no significant binding to the C7 negative control (fourth panel).

Figure 3:
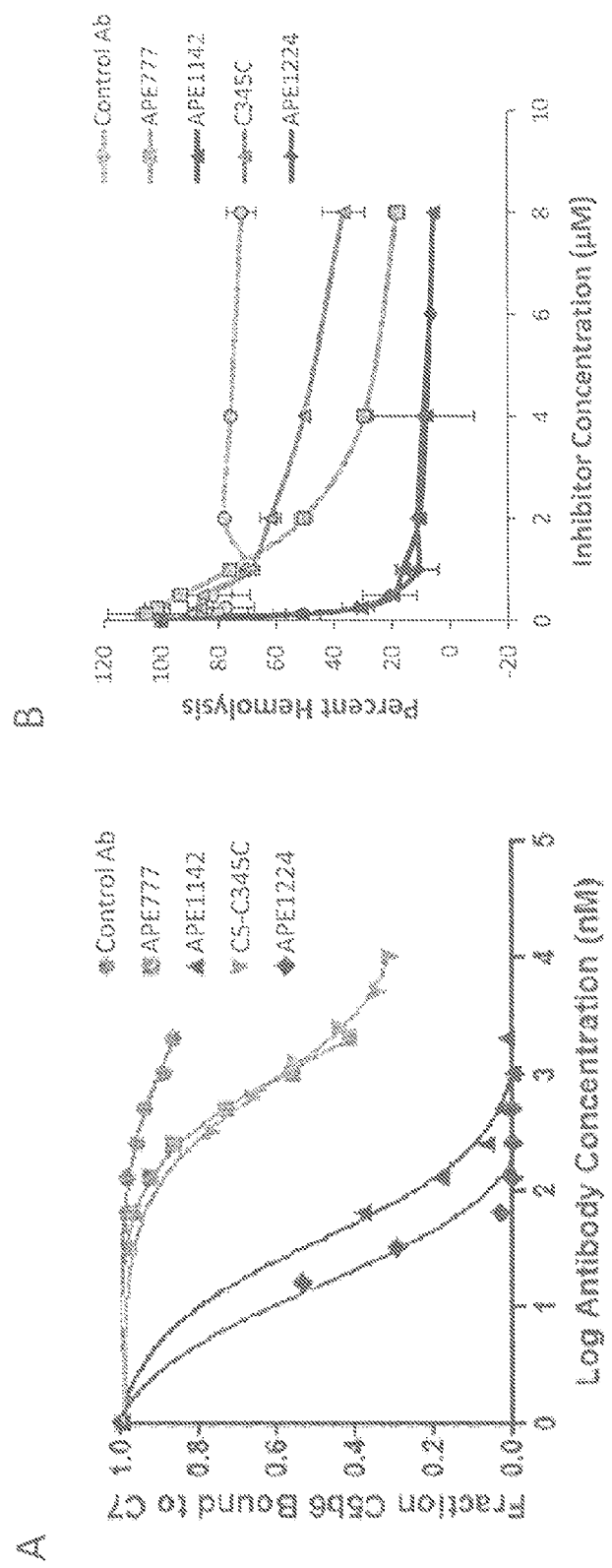

FIG. 3A is a graph which depicts experimental data summarizing the results of the BIACORE™ blocking assay described in Example 3. Varying concentrations of antibody or control protein were incubated with a constant concentration (100 nM) of C5b6, and then flowed over a CM5 surface with C7 captured via an anti-C7 antibody. Fraction C5b6 bound to C7 was calculated by comparing the maximum signal (RU) obtained in the presence and absence of inhibitor.

FIG. 3B is a graph which depicts experimental data illustrating the results of the hemolysis assay described in Example 3. The graph depicts the concentration of antibody, control isotype-matched antibody, or control C5-C345C protein relative to the fraction of red blood cell lysis using 1% serum. Percent specific lysis was normalized to lysis observed in the absence of added inhibitor, control antibody, or control protein.

DETAILED DESCRIPTION OF THE INVENTION

The invention provides an isolated immunoglobulin heavy chain polypeptide and/or an isolated immunoglobulin light chain polypeptide, or a fragment (e.g., antigen-binding fragment) thereof. The term "immunoglobulin" or "antibody," as used herein, refers to a protein that is found in blood or other bodily fluids of vertebrates, which is used by the immune system to identify and neutralize foreign objects, such as bacteria and viruses. The polypeptide is "isolated" in that it is removed from its natural environment. In a preferred embodiment, an immunoglobulin or antibody is a protein that comprises at least one complementarity determining region (CDR). The CDRs form the "hypervariable region" of an antibody, which is responsible for antigen binding (discussed further below). A whole immunoglobulin typically consists of four polypeptides: two identical copies of a heavy (H) chain polypeptide and two identical copies of a light (L) chain polypeptide. Each of the heavy chains contains one N-terminal variable ($V_H$) region and three C-terminal constant ($C_H1$, $C_H2$, and $C_H3$) regions, and each light chain contains one N-terminal variable ($V_L$) region and one C-terminal constant ($C_L$) region. The light chains of antibodies can be assigned to one of two distinct types, either kappa (κ) or lambda (λ), based upon the amino acid sequences of their constant domains. In a typical immunoglobulin, each light chain is linked to a heavy chain by disulphide bonds, and the two heavy chains are linked to each other by disulphide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen binding site of an antibody. The $V_H$ and $V_L$ regions have the same general structure, with each region comprising four framework (FW or FR) regions. The term "framework region," as used herein, refers to the relatively conserved amino acid sequences within the variable region which are located between the hypervariable or complementary determining regions (CDRs). There are four framework regions in each variable domain, which are designated FR1, FR2, FR3, and FR4. The framework regions form the β sheets that provide the structural framework of the variable region (see, e.g., C. A. Janeway et al. (eds.), Immunobiology, 5th Ed., Garland Publishing, New York, N.Y. (2001)).

The framework regions are connected by three complementarity determining regions (CDRs). As discussed above, the three CDRs, known as CDR1, CDR2, and CDR3, form the "hypervariable region" of an antibody, which is responsible for antigen binding. The CDRs form loops connecting, and in some cases comprising part of, the beta-sheet structure formed by the framework regions. While the constant regions of the light and heavy chains are not directly involved in binding of the antibody to an antigen, the constant regions can influence the orientation of the variable regions. The constant regions also exhibit various effector functions, such as participation in antibody-dependent cellular toxicity via interactions with effector molecules and cells.

The isolated immunoglobulin heavy chain polypeptide and the isolated immunoglobulin light chain polypeptide of the invention desirably bind to complement protein C5 (also referred to as "C5 protein," "complement component C5," "complement protein C5," and "C5"). The C5 complement protein is a 190 kD glycoprotein comprised of two disulphide-linked polypeptide chains: alpha (C5a) and beta (C5b) (Tack et al., supra). Activation of the complement system typically occurs as a result of antigen-antibody binding. Upon activation, proteases in the complement system cleave specific proteins to release cytokines, inducing a cascade of further cleavages that ultimately results in the association of the C5b protein with the C6 complement protein and formation of the membrane attack complex (MAC). The MAC is comprised of transmembrane channels on the surface of pathogenic cells (e.g., bacteria cells), which disrupt the phospholipid bilayer of the pathogen cell membrane, thereby leading to cell lysis and death (see, e.g., Peitsch et al., Curr. Opin. Cell Biol., 3(4): 710-716 (1991)). Abnormal activation or expression of the complement system can give rise to a variety of inflammatory disorders, including but not limited to, autoimmune diseases, severe trauma, sepsis, ischemia-reperfusion injury, or systemic inflammatory response syndrome (see, e.g., Trendelenburg, Swiss Med. Wkly., 137: 413-417 (2007)). Abnormal activation of the C5 protein, in particular, has been shown to play a role in the development of age-related macular degeneration, myocardial infarction, coronary artery bypass grafting, hereditary angioedema, paroxysmal nocturnal hemoglubinuria, rheumatoid arthritis, osteoporosis, osteoarthritis, inflammation, and cancer.

Antibodies which bind the complement C5 protein, and components thereof, are known in the art (see, e.g., U.S. Pat. Nos. 7,432,356 and 8,206,716, and Mahaffey et al., Circulation, 108: 1176-1183 (2003)). Anti-C5 antibodies also are commercially available from sources such as, for example, R&D Systems (Minneapolis, Minn.). As discussed above, Eculizumab (SOLIRIS™, Alexion Pharmaceuticals, Inc., Cheshire, Conn.) is a humanized monoclonal antibody approved by the U.S. Food and Drug Administration (FDA) to treat paroxysmal nocturnal hemoglobinuria (PNH) and atypically hemolytic uremic syndrome (aHUS). Pexelizumab is a 25 kD single chain fragment (scFv) of eculizmab, which was designed to treat acute cardiovascular complications (see, e.g., Thomas et al., Mol. Immunol., 33: 1389-1401 (1996); Kaplan M., Curr. Opin. Investig. Drugs, 3: 1017-1023 (2002); and Whiss, P.A., Curr. Opin. Investig. Drugs., 3: 870-877 (2002))

One example of an immunoglobulin heavy chain polypeptide that binds to the complement C5 protein comprises the amino acid sequence of SEQ ID NO: 1. In one embodiment of the invention, the isolated immunoglobulin heavy chain polypeptide comprises or consists of SEQ ID NO: 1, except that (a) one or more of residues 18, 35, 50, and 104 of SEQ ID NO: 1 are replaced with a different residue, and/or (b) residue 56 of SEQ ID NO: 1 is deleted. For example, the isolated immunoglobulin heavy chain polypeptide can comprise SEQ ID NO: 1, except that either (a) one or more of residues 18, 35, 50, and 104 of SEQ ID NO: 1 are replaced with a different residue, or (b) residue 56 of SEQ ID NO: 1 is deleted. Alternatively, the isolated immunoglobulin heavy chain polypeptide can comprise SEQ ID NO: 1, except that both (a) one or more of residues 18, 35, 50, and 104 of SEQ ID NO: 1 are replaced with a different residue, and (b) residue 56 of SEQ ID NO: 1 is deleted. Each of amino acid residues 18, 35, 50, and 104 of SEQ ID NO: 1 can be replaced with any suitable amino acid residue that can be the same or different in each position. For example, the amino acid residue of a first position can be replaced with a first different amino acid residue, and the amino acid residue of a second position can be replaced with a second different amino acid residue, wherein the first and second different amino acid residues are the same or different. An amino acid "replacement" or "substitution" refers to the replacement of one amino acid at a given position or residue by another amino acid at the same position or residue within a polypeptide sequence.

Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

The amino acid replacement or substitution can be conservative, semi-conservative, or non-conservative. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz and Schirmer, *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz and Schirmer, supra).

Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free —NH₂ can be maintained.

"Semi-conservative mutations" include amino acid substitutions of amino acids within the same groups listed above, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

In one embodiment, the isolated immunoglobulin heavy chain polypeptide comprises or consists of SEQ ID NO: 1, except that (a) residue 18 of SEQ ID NO: 1 is replaced with a proline (P) residue, (b) residue 35 of SEQ ID NO: 1 is replaced with a threonine (T) residue, (c) residue 50 of SEQ ID NO: 1 is replaced with a valine (V) residue, (d) residue 104 of SEQ ID NO: 1 is replaced with a lysine (K) residue, or (e) any combination of two or more of the foregoing replacements.

In another embodiment, the isolated immunoglobulin heavy chain polypeptide comprises or consists of SEQ ID NO: 1, except that at least one amino acid residue of SEQ ID NO: 1 is deleted. The deletion of one or more amino acid residues can occur as a result of a deletion mutation introduced into a nucleic acid sequence encoding the inventive amino acid sequence. The term "deletion mutation," as used herein, refers to the removal or loss of one or more nucleotides from a nucleic acid sequence, and is also referred to in the art as a "gene deletion," a "deficiency," or a "deletion." A deletion mutation can be introduced at any suitable location of the nucleic acid sequence encoding the inventive amino acid sequences. For example, a deletion mutation can be introduced into the region of a nucleic acid sequence that encodes the variable region or the constant region of an immunoglobulin heavy or light chain. Preferably, the deletion mutation is introduced into the region of the nucleic acid sequence that encodes the variable region of an immunoglobulin heavy or light chain polypeptide.

Any suitable number of amino acid residues can be deleted from the inventive immunoglobulin heavy chain polypeptide comprising SEQ ID NO: 1. Desirably, 1-10 amino acid residues (e.g., 1, 2, 3, 4, 5, 6, 7, 8, 9, or 10 residues, or a range defined by any two of the foregoing values) can be deleted from SEQ ID NO: 1. In a preferred embodiment, the isolated immunoglobulin heavy chain polypeptide comprises SEQ ID NO: 1, except that residue 56 of SEQ ID NO: 1 is deleted. As discussed above, the inventive immunoglobulin heavy chain polypeptide comprising SEQ ID NO: 1 can include a deletion of residue 56 alone, or in combination with one or more amino acid replacements at residues 18, 35, 50, and/or 104 of SEQ ID NO: 1.

The invention provides an isolated immunoglobulin heavy chain polypeptide which comprises or consists of an amino acid sequence selected from the group consisting of (a) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 2, (b) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 3, (c) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 4, (d) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 5, and an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 27.

Nucleic acid or amino acid sequence "identity," as described herein, can be determined by comparing a nucleic acid or amino acid sequence of interest to a reference nucleic acid or amino acid sequence. The percent identity is the number of nucleotides or amino acid residues that are the same (i.e., that are identical) as between the sequence of interest and the reference sequence divided by the length of the longest sequence (i.e., the length of either the sequence of interest or the reference sequence, whichever is longer). A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FAS™, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA*, 106(10): 3770-3775 (2009), Durbin et al., eds., *Biological Sequence Analysis: Probalistic Models of Proteins and Nucleic Acids*, Cambridge University Press, Cambridge, UK (2009), Soding, *Bioinformatics*, 21(7): 951-960 (2005), Altschul et al., *Nucleic Acids Res.*, 25(17): 3389-3402 (1997), and Gusfield, *Algorithms on Strings, Trees and Sequences*, Cambridge University Press, Cambridge UK (1997)).

Exemplary immunoglobulin heavy chain polypeptides as described above can comprise or consist of any one of the following amino acid sequences: SEQ ID NO: 2, SEQ ID NO: 3, SEQ ID NO: 4, SEQ ID NO: 5, and SEQ ID NO: 27.

The invention also provides an isolated immunoglobulin heavy chain polypeptide which comprises CDR1, CDR2, or CDR3, or any combination of CDR1, CDR2, and/or CDR3 of an amino acid sequence selected from the group consisting of SEQ ID NO: 2, SEQ ID NO: 3, SEQ ID NO: 4, SEQ ID NO: 5, and SEQ ID NO: 27. In one embodiment, the isolated immunoglobulin heavy chain polypeptide comprises only one of CDR1, CDR2 or CDR3 of an amino acid sequence selected from the group consisting of SEQ ID NO: 2, SEQ ID NO: 3, SEQ ID NO: 4, SEQ ID NO: 5, and SEQ ID NO: 27. In another embodiment, the isolated immunoglobulin heavy chain polypeptide comprises CDR1 and CDR2, CDR1 and CDR3, or CDR2 and CDR3 of an amino acid sequence selected from the group consisting of SEQ ID NO: 2, SEQ ID NO: 3, SEQ ID NO: 4, SEQ ID NO: 5, and SEQ ID NO: 27. Alternatively, the isolated immunoglobulin heavy chain polypeptide can comprise CDR1, CDR2, and CDR3 of an amino acid sequence selected from the group consisting of SEQ ID NO: 2, SEQ ID NO: 3, SEQ ID NO: 4, SEQ ID NO: 5, and SEQ ID NO: 27.

One example of an immunoglobulin light chain polypeptide that binds to the complement C5 protein comprises or consists of the amino acid sequence of SEQ ID NO: 6. In one embodiment of the invention, the isolated immunoglobulin light chain polypeptide comprises or consists of SEQ ID NO: 6, except that (a) one or more of residues 31, 54, 69, 79, 81, 93, 94, 96, and 97 of SEQ ID NO: 6 are replaced with a different residue, (b) an amino acid sequence comprising QYGSS (SEQ ID NO: 25) is inserted into SEQ ID NO: 6 after residue 95, (c) an amino acid sequence comprising GGSPEY (SEQ ID NO: 26) is inserted into SEQ ID NO: 6 after residue 98, (d) residue 97 of SEQ ID NO: 6 is deleted, (e) residue 98 of SEQ ID NO: 6 is deleted, or any combination of the aforementioned amino acid replacements, insertions, and/or deletions. In this respect, for example, the isolated immunoglobulin light chain polypeptide can comprise or consist of SEQ ID NO: 6, except that one or more of residues 31, 54, 69, 79, 81, 93, 94, 96, and 97 of SEQ ID NO: 6 are replaced with a different residue, and an amino acid sequence comprising GGSPEY (SEQ ID NO: 26) is inserted into SEQ ID NO: 6 after residue 98. In another embodiment, for example, the isolated immunoglobulin light chain polypeptide can comprise or consist of SEQ ID NO: 6, except that residue 97 of SEQ ID NO: 6 is deleted and residue 98 of SEQ ID NO: 6 is deleted.

In one embodiment, the isolated immunoglobulin light chain polypeptide comprises or consists of SEQ ID NO: 6, except that (a) one or more of residues 31, 54, 69, 79, 81, 93, 94, 96, and 97 of SEQ ID NO: 6 are replaced with a different residue. Each of amino acid residues 31, 54, 69, 79, 81, 93, 94, 96, and 97 of SEQ ID NO: 6 can be replaced with any suitable amino acid residue that can be the same or different in each position. For example, the amino acid residue of a first position can be replaced with a first different amino acid residue, and the amino acid residue of a second position can be replaced with a second different amino acid residue, wherein the first and second different amino acid residues are the same or different.

In another embodiment, the isolated immunoglobulin light chain polypeptide comprises or consists of SEQ ID NO: 6, except that residue 31 of SEQ ID NO: 6 is replaced with an isoleucine (I) residue, (b) residue 54 of SEQ ID NO: 6 is replaced with a threonine (T) residue, (c) residue 69 of SEQ ID NO: 6 is replaced with a valine (V) residue, a glutamic acid (E) residue, or an arginine (R) residue (d) residue 79 of SEQ ID NO: 6 is replaced with an arginine (R) residue, (e) residue 81 of SEQ ID NO: 6 is replaced with an alanine (A) residue, (f) residue 93 of SEQ ID NO: 6 is replaced with an aspartic acid (D) residue, (g) residue 94 of SEQ ID NO: 6 is replaced with an arginine (R) residue, a glycine (G) residue, an isoleucine (I) residue, or a threonine (T) residue, (h) residue 96 of SEQ ID NO: 6 is replaced with an alanine (A) residue, a threonine (T) residue, or a leucine (L) residue, (i) residue 97 of SEQ ID NO: 6 is replaced with an aspartic acid (D) residue, or (j) any combination of (a)-(i).

Exemplary immunoglobulin light chain polypeptides as described above can comprise or consist of any one of the following amino acid sequences: SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 16, SEQ ID NO: 17, SEQ ID NO: 18, SEQ ID NO: 20, SEQ ID NO: 21, and SEQ ID NO: 23.

In one embodiment, the isolated immunoglobulin light chain polypeptide comprises or consists of SEQ ID NO: 6, except that residue 94 of SEQ ID NO: 6 is replaced with an arginine (R) residue, and residue 96 of SEQ ID NO: 6 is replaced with a leucine (L) residue. An example of such an immunoglobulin light chain polypeptide comprises or consists of SEQ ID NO: 15.

In addition, one or more amino acids can be inserted into the aforementioned immunoglobulin light chain polypeptide. Any number of any suitable amino acids can be inserted into the amino acid sequence of the immunoglobulin light chain polypeptide. In this respect, at least one amino acid (e.g., 2 or more, 5 or more, or 10 or more amino acids), but not more than 20 amino acids (e.g., 18 or less, 15 or less, or 12 or less amino acids), can be inserted into the amino acid sequence of the immunoglobulin light chain polypeptide. Preferably, 1-10 amino acids (e.g., 2, 3, 4, 5, 6, 7, 8, or 9 amino acids) are inserted in to the amino acid sequence of the immunoglobulin light chain polypeptide. In this respect, the amino acid(s) can be inserted into SEQ ID NO: 6 in any suitable location. Preferably, the amino acid(s) are inserted into a CDR (e.g., CDR1, CDR2, or CDR3) of SEQ ID NO: 6. In one embodiment, the amino acid(s) are inserted into CDR3 of SEQ ID NO: 6. For example, an amino acid sequence comprising QYGSS (SEQ ID NO: 25) can be inserted into SEQ ID NO: 6 after residue 95. Alternatively or in addition, an amino acid sequence comprising GGSPEY (SEQ ID NO: 26) can be inserted into SEQ ID NO: 6 after residue 96. As discussed above, the inventive immunoglobulin light chain polypeptide comprising or consisting of SEQ ID NO: 6 can include an amino acid insertion alone, or in combination with one or more amino acid replacements and/or deletions described herein. Exemplary immunoglobulin light chain polypeptides as described above can comprise or consist of SEQ ID NO: 19 or SEQ ID NO: 24.

In another embodiment, the isolated immunoglobulin light chain polypeptide comprises or consists of SEQ ID NO: 6, except that at least one amino acid residue of SEQ ID NO: 6 is deleted. Any suitable number of amino acid residues can be deleted from the inventive immunoglobulin light chain polypeptide comprising or consisting of SEQ ID NO: 6. Desirably, 1-10 amino acid residues (e.g., 1, 2, 3, 4, 5, 6, 7, 8, 9, or 10 residues, or a range defined by any two of the foregoing values) are deleted from SEQ ID NO: 6. In a preferred embodiment, the isolated immunoglobulin light chain polypeptide comprises or consists of SEQ ID NO: 6, except that residue 97 of SEQ ID NO: 6 is deleted, residue 98 of SEQ ID NO: 6 is deleted, or both residues 97 and 98 of SEQ ID NO: 6 are deleted. As discussed above, the inventive immunoglobulin light chain polypeptide comprising or consisting of SEQ ID NO: 6 can include a deletion of residues 97 and/or 98 alone, or in combination with one or more amino acid replacements and/or insertions described herein. An example of such an immunoglobulin light chain polypeptide comprises or consists of SEQ ID NO: 22.

The invention provides an isolated immunoglobulin light chain polypeptide which comprises or consists of an amino acid sequence selected from the group consisting of (a) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 7, (b) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 8, (c) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 9, (d) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 10, (e) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 11, (f) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 12, (g) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 13, (h) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 14, (i) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 15, (j) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 16, (k) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 17, (l) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 18, (m) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 19, (n) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 20, (o) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 21, (p) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 22, (q) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 23, and (r) an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 24.

The invention also provides an isolated immunoglobulin light chain polypeptide which comprises CDR1, CDR2, or CDR3, or any combination of CDR1, CDR2, and/or CDR3 of any one of SEQ ID NO: 7-SEQ ID NO: 24. In one embodiment, the isolated immunoglobulin light chain polypeptide comprises only one of CDR1, CDR2 or CDR3 of any one of SEQ ID NO: 7-SEQ ID NO: 24. In another embodiment, the isolated immunoglobulin light chain polypeptide comprises CDR1 and CDR2, CDR1 and CDR3, or CDR2 and CDR3 of any one of SEQ ID NO: 7-SEQ ID NO: 24. Alternatively, the isolated immunoglobulin light chain polypeptide can comprise CDR1, CDR2, and CDR3 of any one of SEQ ID NO: 7-SEQ ID NO: 24.

The invention provides an isolated complement protein C5 (C5)-binding agent comprising or consisting of the inventive isolated amino acid sequences described herein. By "C5-binding agent" is meant a molecule, preferably a proteinaceous molecule, that binds specifically to a complement protein C5. Preferably, the C5-binding agent is an antibody or a fragment (e.g., immunogenic fragment) thereof. The isolated C5-binding agent of the invention comprises or consists of the inventive isolated immunoglobulin heavy chain polypeptide and/or the inventive isolated immunoglobulin light chain polypeptide. In one embodiment, the isolated C5-binding agent comprises or consists of the inventive immunoglobulin heavy chain polypeptide or the inventive immunoglobulin light chain polypeptide. In another embodiment, the isolated C5-binding agent comprises or consists of the inventive immunoglobulin heavy chain polypeptide and the inventive immunoglobulin light chain polypeptide.

The invention is not limited to an isolated C5-binding agent comprising or consisting an immunoglobulin heavy chain polypeptide or light chain polypeptide having replacements, insertions, and/or deletions of the specific amino acid residues disclosed herein. Indeed, any amino acid residue of the inventive immunoglobulin heavy chain polypeptide and/or the inventive immunoglobulin light chain polypeptide can be replaced, in any combination, with a different amino acid residue, or can be deleted or inserted, so long as the biological activity of the C5-binding agent is enhanced or improved as a result of the amino acid replacements, insertions, and/or deletions. The "biological activity" of an C5-binding agent refers to, for example, binding affinity for a particular C5 epitope, neutralization or inhibition of complement C5 protein activity in vivo (e.g., $IC_{50}$), pharmacokinetics, and cross-reactivity (e.g., with non-human homologs or orthologs of the C5 protein, or with other proteins or tissues). Other biological properties or characteristics of an antigen-binding agent recognized in the art include, for example, avidity, selectivity, solubility, folding, immunotoxicity, expression, formulation, and catalytic activity. The aforementioned properties or characteristics can be observed, measured, and/or assessed using standard techniques including, but not limited to, ELISA, competitive ELISA, BIACORE or KINEXA surface plasmon resonance analysis, in vitro or in vivo neutralization assays, receptor binding assays, cytokine or growth factor production and/or secretion assays, complement-mediated hemolysis assays, and signal transduction and immunohistochemistry assays.

The terms "inhibit" or "neutralize," as used herein with respect to the activity of a C5-binding agent, refer to the ability to substantially antagonize, prohibit, prevent, restrain, slow, disrupt, alter, eliminate, stop, or reverse the progression or severity of, for example, the biological activity of the complement C5 protein, or a disease or condition associated with the complement C5 protein. The isolated C5-binding agent of the invention preferably inhibits or neutralizes the activity of the C5 complement protein by at least about 20%, about 30%, about 40%, about 50%, about 60%, about 70%, about 80%, about 90%, about 95%, about 100%, or a range defined by any two of the foregoing values.

The isolated C5-binding agent of the invention can be a whole antibody, as described herein, or an antibody fragment. The terms "fragment of an antibody," "antibody fragment," and "functional fragment of an antibody" are used interchangeably herein to mean one or more fragments of an antibody that retain the ability to specifically bind to an antigen (see, generally, Holliger et al., Nat. Biotech., 23(9): 1126-1129 (2005)). The isolated C5-binding agent can contain any C5-binding antibody fragment. The antibody fragment desirably comprises, for example, one or more CDRs, the variable region (or portions thereof), the constant region (or portions thereof), or combinations thereof. Examples of antibody fragments include, but are not limited to, (i) a Fab fragment, which is a monovalent fragment consisting of the $V_L$, $V_H$, $C_L$, and $CH_1$ domains, (ii) a $F(ab')_2$ fragment, which is a bivalent fragment comprising two Fab fragments linked by a disulfide bridge at the hinge region, and (iii) a Fv fragment consisting of the $V_L$ and $V_H$ domains of a single arm of an antibody.

In embodiments where the isolated C5-binding agent comprises or consists of a fragment of the immunoglobulin heavy chain or light chain polypeptide, the fragment can be of any size so long as the fragment binds to, and preferably inhibits the activity of, complement C5 protein. In this respect, a fragment of the immunoglobulin heavy chain polypeptide desirably comprises between about 5 and 18 (e.g., about 5, 6, 7, 8, 9, 10, 11, 12, 13, 14, 15, 16, 17, 18, or a range defined by any two of the foregoing values) amino acids. Similarly, a fragment of the immunoglobulin light chain polypeptide desirably comprises between about 5 and 18 (e.g., about 5, 6, 7, 8, 9, 10, 11, 12, 13, 14, 15, 16, 17, 18, or a range defined by any two of the foregoing values) amino acids.

When the C5-binding agent is an antibody or antibody fragment, the antibody or antibody fragment comprises a constant region ($F_c$) of any suitable class. Preferably, the antibody or antibody fragment comprises a constant region that is based upon wild-type IgG1, IgG2, or IgG4 antibodies, or variants thereof.

The C5-binding agent also can be a single chain antibody fragment. Examples of single chain antibody fragments include, but are not limited to, (i) a single chain Fv (scFv), which is a monovalent molecule consisting of the two domains of the Fv fragment (i.e., $V_L$ and $V_H$) joined by a synthetic linker which enables the two domains to be synthesized as a single polypeptide chain (see, e.g., Bird et al., Science, 242: 423-426 (1988); Huston et al., Proc. Natl. Acad. Sci. USA, 85: 5879-5883 (1988); and Osbourn et al., Nat. Biotechnol., 16: 778 (1998)) and (ii) a diabody, which is a dimer of polypeptide chains, wherein each polypeptide chain comprises a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a dimeric molecule having two functional antigen binding sites. Antibody fragments are known in the art and are described in more detail in, e.g., U.S. Patent Application Publication 2009/0093024 A1.

The isolated C5-binding agent also can be an intrabody or fragment thereof. An intrabody is an antibody which is expressed and which functions intracellularly. Intrabodies typically lack disulfide bonds and are capable of modulating the expression or activity of target genes through their specific binding activity. Intrabodies include single domain fragments such as isolated $V_H$ and $V_L$ domains and scFvs. An intrabody can include sub-cellular trafficking signals attached to the N or C terminus of the intrabody to allow expression at high concentrations in the sub-cellular compartments where a target protein is located. Upon interaction with a target gene, an intrabody modulates target protein function and/or achieves phenotypic/functional knockout by mechanisms such as accelerating target protein degradation and sequestering the target protein in a non-physiological sub-cellular compartment. Other mechanisms of intrabody-mediated gene inactivation can depend on the epitope to which the intrabody is directed, such as binding to the catalytic site on a target protein or to epitopes that are involved in protein-protein, protein-DNA, or protein-RNA interactions.

The isolated C5-binding agent can be, or can be obtained from, a human antibody, a non-human antibody, or a chimeric antibody. By "chimeric" is meant an antibody or fragment thereof comprising both human and non-human regions. Preferably, the isolated C5-binding agent is a humanized antibody. A "humanized" antibody is a monoclonal antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise, one, two, or three CDRs obtained or derived from a non-human antibody. In a preferred embodiment of the invention, CDRH3 of the inventive C5-binding agent is obtained or derived from a mouse monoclonal antibody, while the remaining variable regions and constant region of the inventive C5-binding agent are obtained or derived from a human monoclonal antibody.

A human antibody, a non-human antibody, a chimeric antibody, or a humanized antibody can be obtained by any means, including via in vitro sources (e.g., a hybridoma or a cell line producing an antibody recombinantly) and in vivo sources (e.g., rodents). Methods for generating antibodies are known in the art and are described in, for example, Köhler and Milstein, *Eur. J. Immunol.*, 5: 511-519 (1976); Harlow and Lane (eds.), *Antibodies: A Laboratory Manual*, CSH Press (1988); and Janeway et al. (eds.), *Immunobiology, 5th Ed.*, Garland Publishing, New York, N.Y. (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™, and the Kyowa Kirin KM-MOUSE™ (see, e.g., Lonberg, *Nat. Biotechnol.*, 23(9): 1117-25 (2005), and Lonberg, *Handb. Exp. Pharmacol.*, 181: 69-97 (2008)). A humanized antibody can be generated using any suitable method known in the art (see, e.g., An, Z. (ed.), *Therapeutic Monoclonal Antibodies: From Bench to Clinic*, John Wiley & Sons, Inc., Hoboken, N.J. (2009)), including, e.g., grafting of non-human CDRs onto a human antibody scaffold (see, e.g., Kashmiri et al., *Methods*, 36(1): 25-34 (2005); and Hou et al., J. Biochem., 144(1): 115-120 (2008)). In one embodiment, a humanized antibody can be produced using the methods described in, e.g., U.S. Patent Application Publication 2011/0287485 A1.

In a preferred embodiment, the C5-binding agent binds an epitope of complement protein C5 which comprises the amino acid sequence of SEQ ID NO: 28. The invention also provides an isolated or purified epitope of complement protein C5, which comprises the amino acid sequence of SEQ ID NO: 28, and is encoded by a nucleic acid sequence comprising SEQ ID NO: 29.

The invention also provides one or more isolated nucleic acid sequences that encode the inventive immunoglobulin heavy chain polypeptide, the inventive immunoglobulin light chain polypeptide, and the inventive isolated C5-binding agent.

The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

The invention further provides a vector comprising one or more nucleic acid sequences encoding the inventive immunoglobulin heavy chain polypeptide, the inventive immunoglobulin light chain polypeptide, and/or the inventive C5-binding agent. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual, 3rd edition*, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994)).

In addition to the nucleic acid sequence encoding the inventive immunoglobulin heavy polypeptide, the inventive immunoglobulin light chain polypeptide, and/or the inventive C5-binding agent, the vector preferably comprises expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include, for example, the Tet system (U.S. Pat. Nos. 5,464,758 and 5,814,618), the Ecdysone inducible system (No et al., *Proc. Natl. Acad. Sci.*, 93: 3346-3351 (1996)), the T-REX™ system (Invitrogen, Carlsbad, Calif.), LACSWITCH™ system (Stratagene, San Diego, Calif.), and the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715; and Kramer & Fussenegger, *Methods Mol. Biol.*, 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences.

The vector also can comprise a "selectable marker gene." The term "selectable marker gene," as used herein, refers to a nucleic acid sequence that allow cells expressing the nucleic acid sequence to be specifically selected for or against, in the presence of a corresponding selective agent. Suitable selectable marker genes are known in the art and described in, e.g., International Patent Application Publications WO 1992/008796 and WO 1994/028143; Wigler et al., *Proc. Natl. Acad. Sci. USA*, 77: 3567-3570 (1980); O'Hare et al., *Proc. Natl. Acad. Sci. USA*, 78: 1527-1531 (1981); Mulligan & Berg, *Proc. Natl. Acad. Sci. USA*, 78: 2072-2076 (1981); Colberre-Garapin et al., *J. Mol. Biol.*, 150:1-14 (1981); Santerre et al., *Gene*, 30: 147-156 (1984); Kent et al., *Science*, 237: 901-903 (1987); Wigler et al., *Cell*, 11: 223-232 (1977); Szybalska & Szybalski, *Proc. Natl. Acad. Sci. USA*, 48: 2026-2034 (1962); Lowy et al., *Cell*, 22: 817-823 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy*, 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNA™ 5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), and pCI or pFN10A (ACT) FLEXI™ from Promega (Madison, Wis.).

Viral vectors also can be used. Representative commercially available viral expression vectors include, but are not limited to, the adenovirus-based PER.C6™ system available from Crucell, Inc. (Leiden, The Netherlands), the lentiviral-based pLP1 from Invitrogen (Carlsbad, Calif.), and the retroviral vectors pFB-ERV plus pCFB-EGSH from Stratagene (La Jolla, Calif.).

Nucleic acid sequences encoding the inventive amino acid sequences can be provided to a cell on the same vector (i.e., in cis). A unidirectional promoter can be used to control expression of each nucleic acid sequence. In another embodiment, a combination of bidirectional and unidirectional promoters can be used to control expression of multiple nucleic acid sequences. Nucleic acid sequences encoding the inventive amino acid sequences alternatively can be provided to the population of cells on separate vectors (i.e., in trans). Each of the nucleic acid sequences in each of the separate vectors can comprise the same or different expression control sequences. The separate vectors can be provided to cells simultaneously or sequentially.

The vector(s) comprising the nucleic acid(s) encoding the inventive amino acid sequences can be introduced into a host cell that is capable of expressing the polypeptides encoded thereby, including any suitable prokaryotic or eukaryotic cell. Preferred host cells are those that can be easily and reliably grown, have reasonably fast growth rates, have well characterized expression systems, and can be transformed or transfected easily and efficiently.

Examples of suitable prokaryotic cells include, but are not limited to, cells from the genera *Bacillus* (such as *Bacillus subtilis* and *Bacillus brevis*), *Escherichia* (such as *E. coli*), *Pseudomonas*, *Streptomyces*, *Salmonella*, and *Erwinia*. Particularly useful prokaryotic cells include the various strains of *Escherichia coli* (e.g., K12, HB101 (ATCC No. 33694), DH5α, DH10, MC1061 (ATCC No. 53338), and CC102).

Preferably, the vector is introduced into a eukaryotic cell. Suitable eukaryotic cells are known in the art and include, for example, yeast cells, insect cells, and mammalian cells. Examples of suitable yeast cells include those from the genera *Kluyveromyces*, *Pichia*, *Rhino-sporidium*, *Saccharomyces*, and *Schizosaccharomyces*. Preferred yeast cells include, for example, *Saccharomyces cerivisae* and *Pichia pastoris*.

Suitable insect cells are described in, for example, Kitts et al., *Biotechniques*, 14: 810-817 (1993); Lucklow, *Curr. Opin. Biotechnol.*, 4: 564-572 (1993); and Lucklow et al., *J. Virol.*, 67: 4566-4579 (1993). Preferred insect cells include Sf-9 and HIS (Invitrogen, Carlsbad, Calif.).

Preferably, mammalian cells are utilized in the invention. A number of suitable mammalian host cells are known in the art, and many are available from the American Type Culture Collection (ATCC, Manassas, Va.). Examples of suitable mammalian cells include, but are not limited to, Chinese hamster ovary cells (CHO) (ATCC No. CCL61), CHO DHFR-cells (Urlaub et al., *Proc. Natl. Acad. Sci. USA*, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of cells are known in the art.

Most preferably, the mammalian cell is a human cell. For example, the mammalian cell can be a human lymphoid or lymphoid derived cell line, such as a cell line of pre-B lymphocyte origin. Examples of human lymphoid cells lines include, without limitation, RAMOS(CRL-1596), Daudi (CCL-213), EB-3 (CCL-85), DT40 (CRL-2111), 18-81 (Jack et al., *Proc. Natl. Acad. Sci. USA*, 85: 1581-1585 (1988)), Raji cells (CCL-86), and derivatives thereof.

A nucleic acid sequence encoding the inventive amino acid sequence may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology*, Vol. 7, *Gene Transfer and Expression Protocols*, Humana Press (1991)); DEAE-dextran; electroporation; cationic liposome-mediated transfection; tungsten particle-facilitated microparticle bombardment (Johnston, *Nature*, 346: 776-777 (1990)); and strontium phosphate DNA co-precipitation (Brash et al., *Mol. Cell. Biol.*, 7: 2031-2034 (1987)). Phage or viral vectors can be introduced into host cells, after growth of infectious particles in suitable packaging cells, many of which are commercially available.

The invention provides a composition comprising the inventive immunoglobulin heavy chain polypeptide, the inventive immunoglobulin light chain polypeptide, the inventive C5-binding agent, or the inventive vector comprising a nucleic acid sequence encoding any of the foregoing. Preferably, the composition is a pharmaceutically acceptable (e.g., physiologically acceptable) composition, which comprises a carrier, preferably a pharmaceutically acceptable (e.g., physiologically acceptable) carrier, and the inventive amino acid sequences, antigen-binding agent, or vector. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., Remington: *The Science and Practice of Pharmacy*, 21*st* *Edition*, Lippincott Williams & Wilkins, Philadelphia, Pa. (2001).

The invention further provides a method of treating a C5-mediated disorder in a mammal. The method comprises administering the aforementioned composition to a mammal having a C5-mediated disorder, whereupon the C5-mediated disorder is treated in the mammal. The term "C5-mediated disorder," as used herein, refers to any disease or disorder in which the presence of the complement C5 protein, or improper regulation of MAC formation, causes or contributes to the pathological effects of the disease, or a decrease in C5 protein levels or activity has a therapeutic benefit in mammals, preferably humans. Examples of C5-mediated diseases include, but are not limited to, age-related macular degeneration, myocardial infarction, coronary artery bypass grafting, hereditary angioedema, paroxysmal nocturnal hemoglubinuria, rheumatoid arthritis, osteoporosis, osteoarthritis, inflammation, and cancer.

As used herein, the terms "treatment," "treating," and the like refer to obtaining a desired pharmacologic and/or physiologic effect. Preferably, the effect is therapeutic, i.e., the effect partially or completely cures a disease and/or adverse symptom attributable to the disease. To this end, the inventive method comprises administering a "therapeutically effective amount" of the C5-binding agent. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the C5-binding agent to elicit a desired response in the individual. For example, a therapeutically effective amount of a C5-binding agent of the invention is an amount which decreases complement C5 protein bioactivity in a human (e.g., by blocking MAC formation).

Alternatively, the pharmacologic and/or physiologic effect may be prophylactic, i.e., the effect completely or partially prevents a disease or symptom thereof. In this respect, the inventive method comprises administering a "prophylactically effective amount" of the C5-binding agent. A "prophylactically effective amount" refers to an amount effective, at dosages and for periods of time necessary, to achieve a desired prophylactic result (e.g., prevention of disease onset).

A typical dose can be, for example, in the range of 1 pg/kg to 20 mg/kg of animal body weight; however, doses below or above this exemplary range are within the scope of the invention. The daily parenteral dose can be about 0.00001 µg/kg to about 20 mg/kg of total body weight (e.g., about 0.001 µg/kg, about 0.1 µg/kg, about 1 µg/kg, about 5 µg/kg, about 10 µg/kg, about 100 µg/kg, about 500 µg/kg, about 1 mg/kg, about 5 mg/kg, about 10 mg/kg, or a range defined by any two of the foregoing values), preferably from about 0.1 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values), more preferably from about 1 µg/kg to 5 mg/kg of total body weight (e.g., about 3 µg/kg, about 15 µg/kg, about 75 µg/kg, about 300 µg/kg, about 900 µg/kg, about 2 mg/kg, about 4 mg/kg, or a range defined by any two of the foregoing values), and even more preferably from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values). Therapeutic or prophylactic efficacy can be monitored by periodic assessment of treated patients. For repeated administrations over several days or longer, depending on the condition, the treatment is repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

The composition comprising the C5-binding agent of the invention can be administered to a mammal using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

Once administered to a mammal (e.g., a human), the biological activity of the inventive C5-binding agent can be measured by any suitable method known in the art. For example, the biological activity can be assessed by determining the stability of a particular C5-binding agent. In one embodiment of the invention, the C5-binding agent (e.g., an antibody) has an in vivo half life between about 15 minutes and 45 days (e.g., about 15 minutes, about 30 minutes, about 1 hour, about 6 hours, about 10 hours, about 12 hours, about 1 day, about 5 days, about 10 days, about 15 days, about 25 days, about 35 days, about 40 days, about 45 days, or a range defined by any two of the foregoing values). In one embodiment, the C5-binding agent can have an in vivo half life between about 2 hours and 20 days (e.g., about 5 hours, about 10 hours, about 15 hours, about 20 hours, about 2 days, about 3 days, about 7 days, about 12 days, about 14 days, about 17 days, about 19 days, or a range defined by any two of the foregoing values). In another embodiment, the C5-binding agent can have an in vivo half life between about 10 days and about 40 days (e.g., about 10 days, about 13 days, about 16 days, about 18 days, about 20 days, about 23 days, about 26 days, about 29 days, about 30 days, about 33 days, about 37 days, about 38 days, about 39 days, about 40 days, or a range defined by any two of the foregoing values). The biological activity of a particular C5-binding agent also can be assessed by determining its binding affinity to a complement C5 protein or an epitope thereof. The term "affinity" refers to the equilibrium constant for the reversible binding of two agents and is expressed as the dissociation constant ($K_D$). Affinity of a binding agent to a ligand, such as affinity of an antibody for an epitope, can be, for example, from about 1 picomolar (pM) to about 1 micromolar (μM) (e.g., from about 1 picomolar (pM) to about 1 nanomolar (nM), or from about 1 nM to about 1 micromolar (μM)). In one embodiment, the C5-binding agent can bind to the complement C5 protein with a $K_D$ less than or equal to 1 nanomolar (e.g., 0.9 nM, 0.8 nM, 0.7 nM, 0.6 nM, 0.5 nM, 0.4 nM, 0.3 nM, 0.2 nM, 0.1 nM, 0.05 nM, 0.025 nM, 0.01 nM, 0.001 nM, or a range defined by any two of the foregoing values). In another embodiment, the C5-binding agent can bind to C5 with a $K_D$ less than or equal to 200 pM (e.g., 190 pM, 175 pM, 150 pM, 125 pM, 110 pM, 100 pM, 90 pM, 80 pM, 75 pM, 60 pM, 50 pM, 40 pM, 30 pM, 25 pM, 20 pM, 15 pM, 10 pM, 5 pM, 1 pM, or a range defined by any two of the foregoing values). Immunoglobulin affinity for an antigen or epitope of interest can be measured using any art-recognized assay. Such methods include, for example, fluorescence activated cell sorting (FACS), separable beads (e.g., magnetic beads), antigen panning, and/or ELISA (see, e.g., Janeway et al. (eds.), *Immunobiology*, 5th ed., Garland Publishing, New York, N.Y., 2001).

The C5-binding agent of the invention may be administered alone or in combination with other drugs (e.g., as an adjuvant). For example, the C5-binding agent can be administered in combination with other agents for the treatment or prevention of the C5-mediated diseases disclosed herein. In this respect, the C5-binding agent can be used in combination with analgesics, opioids, anti-inflammatory agents, chemotherapeutic agents, and/or non-steroidal anti-inflammatory drugs (e.g., acetaminophen, ibuprofen, hydrocodone, fentanyl, oxycodone, oxycontin, buprenorphine, pethidine, diamorphine, methadone, pentazocine, dextromoramide, dipipanone, amitriptyline, COX-2 inhibitors, ketoprofen, piroxicam, gabapentin, orphenadrine, cyclobenzaprine, trazodone, clonidine, celecoxib, duloxetine, cannabis, pregabalin, and axomadol).

In addition to therapeutic uses, the C5-binding agent described herein can be used in diagnostic or research applications. In this respect, the C5-binding agent can be used in a method to diagnose a C5-mediated disease or disorder. In a similar manner, the C5-binding agent can be used in an assay to monitor complement C5 protein levels in a subject being tested for a C5-mediated disease or disorder. Research applications include, for example, methods that utilize the C5-binding agent and a label to detect complement C5 protein in a sample, e.g., in a human body fluid or in a cell or tissue extract. The C5-binding agent can be used with or without modification, such as covalent or non-covalent labeling with a detectable moiety. For example, the detectable moiety can be a radioisotope (e.g., 3H, 14C, 32P, 35S, or 125I), a fluorescent or chemiluminescent compound (e.g., fluorescein isothiocyanate, rhodamine, or luciferin), or an enzyme (e.g., alkaline phosphatase, beta-galactosidase, or horseradish peroxidase). Any method known in the art for separately conjugating an antigen-binding agent (e.g., an antibody) to a detectable moiety may be employed in the context of the invention (see, e.g., Hunter et al., *Nature*, 194: 495-496 (1962); David et al., *Biochemistry*, 13: 1014-1021 (1974); Pain et al., *J. Immunol. Meth.*, 40: 219-230 (1981); and Nygren, *J. Histochem. and Cytochem.*, 30: 407-412 (1982)).

Complement C5 protein levels can be measured using the inventive C5-binding agent by any suitable method known in the art. Such methods include, for example, ELISA, radioimmunoassay (RIA), and FACS. Normal or standard expression values of complement C5 protein can be established using any suitable technique, e.g., by combining a sample comprising, or suspected of comprising, a C5 polypeptide with a C5-specific antibody under conditions suitable to form an antigen-antibody complex. The antibody is directly or indirectly labeled with a detectable substance to facilitate detection of the bound or unbound antibody. Suitable detectable substances include various enzymes, prosthetic groups, fluorescent materials, luminescent materials, and radioactive materials (see, e.g., Zola, *Monoclonal Antibodies: A Manual of Techniques*, CRC Press, Inc. (1987)). The amount of C5 polypeptide expressed in a sample is then compared with the standard values.

The C5-binding agent can be provided in a kit, i.e., a packaged combination of reagents in predetermined amounts with instructions for performing a diagnostic assay. If the C5-binding agent is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

The following examples further illustrate the invention but, of course, should not be construed as in any way limiting its scope.

EXAMPLE 1

This example demonstrates a method of generating a humanized antibody directed against the complement C5 protein (an "anti-C5 antibody").

C5-C345C (SEQ ID NO: 28) is a peptide comprising the C-terminal 147 amino acid residues of the 1648 residue C5 protein, which have been shown experimentally to initiate MAC formation via contacts with complement proteins C6 and C7 (see, e.g., Bramham et al., *J. Biol. Chemistry*, 280: 10636-10645 (2005)). Three female BALB/c mice aged 6-8 weeks were immunized with 0.005 mg of sterile-filtered C5-C345C in PBS together with alhydrogel/muramic dipeptide (ALD/MDP) adjuvant. The C345C-adjuvant mixture was injected into the foot pad of each mouse with a 26-gauge needle. Bi-weekly immunizations were evenly spaced over the course of 28 days. Mice were bled from the tail vein before injections, and blood was stored at −20° C. for further analysis. Mice were euthanized, spleen and draining (popliteal)

lymph nodes were harvested, and cell pellets were resuspended in RNAZOL™ for further analysis (Antibody Solutions, Sunnyvale, Calif.).

Spleen and lymph node cells were lysed and total RNA isolated using the RNEASY™ RNA isolation kit according to the manufacturer's protocol (Qiagen, Valencia, Calif.). Reverse transcription from total RNA was performed by RT-PCR using a combination of random decamers and oligo(dT) primers and 2 µg total RNA according to the manufacturer's protocol of the RETROSCRIPT™ Kit (Ambion). Following cDNA synthesis, immunoglobulin heavy chain (HC) D(J) regions, encoding CDR3 regions (CDRH3), were amplified and gel purified. This amplified CDRH3 diversity was then inserted into nine human heavy chain (HC) germline V-regions (IGHV1-2, 1-69, 3-7, 3-23, 3-30-3, 4-34, 4-59, 5-51, and 6-1), shown in FIG. 1, which were selected based on their frequency of usage in vivo. Full-length IgGs were assembled using IgHC-γ1 and IgKC constant domains. The C-terminal end of the HC was modified with a transmembrane domain to enable cell surface expression (Bowers et al., Proc. Natl. Acad. Sci. USA, 108: 20455-20460 (2011)). The HC library DNAs were pooled into four separate sub-libraries for transfection, each containing two to three germline IGHV templates.

A light chain (LC) sub-library was generated which consisted of five germline Vκ-regions (IGKV1-33, 1D-39, 2D-30, 3-20, and 4-1) fused to J-region sequences, which were also isolated from pooled peripheral blood mononuclear cells (PBMCs) from normal human donors and selected based on their in vivo usage frequency (see., e.g., Bowers et al., Proc. Natl. Acad. Sci. USA, 108: 20455-20460 (2011)).

To isolate C5-C345C-specific binders, each of the four HC sub-library pools was transfected in combination with the five pooled LC libraries into HEK 293 c18 cells, stably selected, and expanded to 1×10$^9$ cells.

After selecting for stable episomal expression, the four HC sub-libraries were each expanded and subjected to iterative rounds of AID-induced mutation and selection by FACS using multimerized, fluorescently labeled antigen to create high avidity binding conditions. Selective pressure for high level expression of IgG was maintained by 2-dimensional sorting with both fluorescently labeled antigen and anti-human IgG labeled with a complementary fluorescent dye. Specifically, binding analysis was performed prior to each round of FACS in order to determine the optimal antigen concentration for selection. Antibody-transfected cells were incubated with various concentrations of C5-C345C-Myc for 0.5 hours at 4° C. Dylight-649-labeled mouse anti-Myc (AbCam) was added at a 2:1 (antigen:anti-Myc antibody) molar ratio, and cells were incubated for 0.5 hours at 4° C. To stain for IgG expression, FITC-AFFINIPURE™ Fab Fragment Goat anti-Human IgG (H+L) (Jackson ImmunoResearch) was added (1:500) for 0.5 hours at 4° C. Cells were pelleted and resuspended in 0.3 mL of DAPI (4',6-diamidino-2-phenylindole dihydrochloride, Sigma-Aldrich, St. Louis, Mo.) solution; 0.2 µg/mL in PBS, 0.1% BSA); and then analyzed for fluorescence on a BD Influx cell sorter (BD Biosciences, San Jose, CA). Antibody-expressing HEK 293 c18 cells (5×10$^7$ in 20 mL PBS, 0.1% BSA) were incubated with a selected concentration of C5-C345 C-Myc for 0.5 hours at 4° C. for cell sorting. Dylight-649-labeled mouse anti-Myc and FITC-labeled goat anti-human IgG Fc were added to the cells as described above. Cells were then resuspended in 1.0 ml DAPI solution (0.2 µg/mL in PBS, 0.1% BSA) and sorted for the strongest antigen-binding cells, relative to level of antibody expression, on a BD Influx cell sorter.

By the third round of sorting, an emerging cell population was identified that expressed antibodies binding to C5-C345C from sub-library 3, derived from constructs using V-regions IGHV3-30-3 and IGHV4-34, as shown in FIG. 2A. Sorts were continued with increased stringency by decreasing the concentration of C5-C345C antigen used to stain cells prior to each round of FACS. A corresponding enrichment of cell populations exhibiting improved C5-C345C binding appeared at each round of FACS, as shown in FIG. 2A.

To identify antigen-specific HC/LC pairs capable of binding complement protein C5, single cell clones from the enriched cell population were isolated by FACS into 96-well plates, and the binding kinetics for each was characterized by BIACORE™ analysis (GE Healthcare, Piscataway, N.J.). Secreted antibody from the cell growth media was captured on the surface of a CM5 chip containing immobilized anti-human Fc antibody, with varying concentrations of C5-C345C analyte. Capture-adjusted report points for each sensorgram, depicted in FIG. 2B, identified antibodies with the most antigen bound per unit antibody (binding late) and slowest off-rates (stability late), indicative of better binding. Of the 176 clones screened, supernatants from 25 of the highest affinity clones were further characterized by BIACORE™ analysis, and 18 of the strongest binders were sequenced to identify eight unique HC/LC pairs. Unique clones were further analyzed based on binding kinetics for C5 domain C5-C345C, binding to the full-length C5 protein, binding to the activated C5bC6 complex, and absence of binding to a C7 negative control. Clone APE777, comprising a heavy chain polypeptide comprising SEQ ID NO: 1 and a light chain polypeptide comprising SEQ ID NO: 6, was found to bind C5-C345C with an affinity of approximately 200 nM, to bind C5 with approximately 10-fold reduced affinity, and to have minimal binding to activated C5b6. Binding to C7 was undetectable, as shown in FIG. 2C.

The results of this example confirm the production of a humanized anti-C5 monoclonal antibody in accordance with the invention.

EXAMPLE 2

This example describes a method of affinity maturing nucleic acid sequences encoding humanized anti-C5 monoclonal antibodies.

Plasmids containing nucleic acid sequences encoding the isolated HC/LC pair of the antibody APE777 (see Example 1) were transfected with a plasmid encoding activation-induced cytidine deaminase (AID) for in vitro affinity maturation by somatic hypermutation in the mammalian cell display system described in Example 1. Following induction of somatic hypermutation via expression of AID, cells expressing higher affinity variants of the starting antibody were isolated by iterative rounds of FACS sorting using decreasing concentrations of fluorescently labeled C5-C345C, with approximately 0.5% of the brightest cells collected at each round. Early rounds of sorting for each strategy were carried out at low nM concentrations of C5-C345C under avid binding conditions. Starting in round three, antibody affinities for C5-C345C in each strategy were sufficiently improved to use directly labeled monovalent antigen without binding avidity (C5-C345C-Dylight-650). Affinity maturation was first observed in FACS scatter plots by the third and fourth rounds of selection for both strategies, and continued through round eight using a final concentration of 100 pM C5-C345C.

Samples from the evolving antibody populations were sequenced to identify enriching mutations over the course of affinity maturation in both strategies, and the observed mutations are summarized in Table 1.

TABLE 1

| Observed mutations | Chain | Strategy | Enriched in round[1] | Observed in post-R3 next generation sequencing (NGS) |
|---|---|---|---|---|
| L18P | HC | A | 4 | + |
| S35T | HC | A/B | 4/5 | + |
| A50V | HC | A/B | 4/5 | + |
| Delete G56 | HC | B | 4 | + |
| N104K | HC | B | 5 | + |
| S31I | LC | A | 8 | + |
| S54T | LC | A | | + |
| G69V | LC | A | | + |
| G69E | LC | A | | + |
| G69R | LC | A | | + |
| L79R | LC | B | | + |
| P81A | LC | A | | + |
| G93D | LC | B | 3 | − |
| S94R | LC | A | 7 | + |
| S94G | LC | A | | + |
| S94I | LC | B | 7 | + |
| S94T | LC | A | | + |
| +QYGSS after S95 | LC | A | 5 | + |
| P96A | LC | B | 4 | + |
| P96L | LC | A | 5 | + |
| Delete E97 and Y98 | LC | A | | + |
| E97D | LC | A | | + |
| P96T | LC | B | 5 | + |
| +GGSPEY after Y98 | LC | B | 7 | + |

[1]Enrichment observed by Sanger sequencing of 40 HC and LC variable regions post-sort round. Mutation was only observed by NGS if no round is indicated.

The majority of mutations were observed in the light chain (LC), beginning with the CDRL3 mutation, G93D, which was enriched in the third round. Two heavy chain (HC) mutations, S35T and A50V, were detected as enriched sequences in the fourth round of both strategies. A single residue deletion of G56 in the CDRH2 emerged in strategy B at round 4. LC mutations in strategy A included P96L, S94R, and a five amino acid insertion, QYGSS (SEQ ID NO: 25), after position 95 in the CDRL3. LC mutations in strategy B included P96A, S94I, and a six amino acid insertion, GSSPEY (SEQ ID NO: 26) after position 98 in the CDRL3. BIACORE™ analysis was used to evaluate C5-C345C binding affinity of isolated clones throughout the maturation process.

Mutations observed in strategies A and B were directly recombined by overlap extension PCR into a 576-member combinatorial library for transfection and expression in 96-well format. BIACORE™ screening identified several clones with low nanomolar affinity for C5-C345C, and one clone, designated APE1224, exhibited a 200 pM binding affinity and represented a 1000-fold improvement in $K_D$ over APE777. APE1224 contains a heavy chain polypeptide comprising two mutations (S35T and a deletion of G56; SEQ ID NO: 3) and a light chain polypeptide comprising two mutations (S94R and P96L; SEQ ID NO: 15).

The results of this example confirm that AID-dependent affinity maturation of a humanized anti-C5 antibody can be used to improve antibody affinity for the complement C5 protein.

EXAMPLE 3

This example demonstrates that the anti-C5 monoclonal antibodies described herein can inhibit the biological activity of the complement C5 protein.

A BIACORE™-based blocking assay was developed to assess the functional activity of the anti-C5-C345C antibodies described above. Formation of the membrane attack complex (MAC) of complement involves proteolytic cleavage of the C5 protein to C5a and C5b, followed by sequential binding of activated C5b to complement C6, C7, C8, and C9 proteins (see, e.g., Muller-Eberhard, Ann. Rev. Immunol., 4: 503-528 (1986)). C5b first reacts the complement protein C6 to form an intermediate complex (C5bC6), followed by irreversible binding of C5bC6 to C7 to form the C5b-7 complex. Antibodies targeting the C5interaction domain C5-C345C are expected to block binding of C5b6 to C7 and subsequent MAC assembly. In this assay, the surface of a series S CM5 chip was immobilized with 3,000 RU of anti-C7 capture antibody (Complement Technology, Inc., Tyler, Tex.). Complement protein C7 at 100 µg/ml (Complement Technology, Inc., Tyler, Tex.) was captured for 60 seconds at 10 µL/min. Antibodies or C5-C345C, over a concentration range with 2-fold dilutions from 2 µM to 62.5 nM or 500 nM to 15.6 nM, as indicated, were incubated with a constant 100 nM concentration of C5b6 and then flowed over the captured C7 surface. Fraction C5b6 bound to C7 was then calculated by dividing the maximum signal (RU) for each sample by that obtained for C5b6 binding to C7 alone. To determine inhibition constants ($K_i$) of antibody variants, normalized data were fit by a three-parameter inhibition curve using GRAPH-PAD™ Prism (GraphPad Software, San Diego, Calif.). The results of this assay are shown in FIG. 3A. The APE777 antibody (described in Example 1), demonstrated modest blocking activity with an inhibition constant, $K_i$, of 41 nM, but did not completely inhibit the C5bC6/C7 interaction at a 2 µM concentration. The affinity-matured anti-C5-C345C variants APE1142 and APE1224 exhibited significantly improved blocking activity, with Ki values of 930 pM and 370 pM, respectively. APE1224 contains a heavy chain polypeptide comprising two mutations (S35T and a deletion of G56; SEQ ID NO: 3) and a light chain polypeptide comprising two mutations (S94R and P96L; SEQ ID NO: 15). APE1142 contains a heavy chain polypeptide comprising three mutations (S35T, A50V, and a deletion of G56; SEQ ID NO: 27) and a light chain polypeptide comprising one mutation (P96A; SEQ ID NO: 20).

To further illustrate functional activity, anti-C5-C345C antibody variants were tested for their ability to inhibit hemolysis of antibody-coated sheep erythrocytes mediated by the classical complement pathway. Recombinant C5-C345, APE777 parental antibody, APE1142 and APE1224 affinity matured antibodies, or an isotype matched control antibody were diluted 2-fold in a round-bottom 96-well plate in the presence of 1% normal human serum (Complement Technology, Inc., Tyler, Tex.). Rabbit antibody-sensitized sheep erythrocytes ($1.25 \times 10^7$ cells in 25 µL; Complement Technology, Inc., Tyler, Tex.) were added to each well, and plates were incubated at 37° C. for 45 minutes on a plate shaker. Reactions were quenched with 100 µL ice cold GVB++(0.1% gelatin, 5 mM Veronal, 145 mM NaCl, 0.025% $NaN_3$, 0.15 mM calcium chloride, 0.5 mM magnesium chloride, pH 7.3; Complement Technology, Inc., Tyler, Tex.), plates were centrifuged at 1250×G for five minutes, and supernatants were assessed for hemoglobin release by reading $OD_{450}$ using a SPECTRAMAX™ absorbance reader (Molecular Devices, Sunnyvale, Calif.). All reagents were diluted in GVB++buffer, and each sample was independently assayed in triplicate.

The results of this assay are shown in FIG. 3B. Percent specific lysis was determined as the amount of erythrocyte lysis relative to lysis in the absence of inhibitor antibody or protein. Hemolysis was weakly inhibited by C5-C345C over the indicated concentration range. Anti-C5-C345C antibody APE777 reached complete inhibition at 8 µM, and was a stronger inhibitor than C5-C345C. The affinity-matured APE1142 and APE1224 variants were stronger inhibitors than APE777, both reaching complete inhibition of complement-mediated lysis in this assay at a concentration of 1 µM.

The results of this example confirm that humanized anti-C5 monoclonal antibodies produced in accordance with the invention are capable of inhibiting the biological activity of complement C5 protein.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated immunoglobulin heavy chain polypeptide which comprises an amino acid sequence of SEQ ID NO: 2, SEQ ID NO: 3, SEQ ID NO: 4, SEQ ID NO: 5, or SEQ ID NO: 27.

2. An isolated immunoglobulin light chain polypeptide, which comprises an amino acid sequence of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

3. An isolated complement protein C5 (C5)-binding antibody, or antigen binding fragment thereof, comprising (a) an isolated immunoglobulin heavy chain polypeptide which comprises an amino acid sequence of SEQ ID NO: 2, SEQ ID NO: 3, SEQ ID NO: 4, SEQ ID NO: 5, or SEQ ID NO: 27, and (b) an isolated immunoglobulin light chain polypeptide which comprises an amino acid sequence of SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

4. The isolated C5-binding antibody of claim 3, which is a F(ab')2, Fab', Fab, Fv, scFv, dsFv, dAb, or a single chain binding polypeptide.

5. The isolated C5-binding antibody of claim 3, which binds to an epitope of complement protein C5 which comprises the amino acid sequence of SEQ ID NO: 28.

6. A composition comprising the isolated C5-binding antibody of claim 3, or antigen binding fragment thereof, and a pharmaceutically acceptable carrier.

7. A method of treating a C5-mediated disorder in a mammal, which method comprises administering an effective amount of the composition of claim 6 to a mammal having an C5-mediated disorder, whereupon the C5-mediated disorder is treated in the mammal.

8. The method of claim 7, wherein the C5-mediated disorder is age-related macular degeneration, myocardial infarction, coronary artery bypass grafting, hereditary angioedema, paroxysmal nocturnal hemoglubinuria, rheumatoid arthritis, osteoporosis, osteoarthritis, inflammation, or cancer.

9. The method of claim 7, wherein the half-life of the C5-binding antibody, or antigen binding fragment thereof, in the mammal is between 15 minutes and 45 days.

10. The method of claim 7, wherein the C5-binding antibody, or antigen binding fragment thereof, binds to C5 with a $K_D$ between about 1 picomolar (pM) and 1 micromolar (μM).

11. The isolated immunoglobulin heavy chain polypeptide of claim 1, which comprises the amino acid sequence of SEQ ID NO: 2.

12. The isolated immunoglobulin heavy chain polypeptide of claim 1, which comprises the amino acid sequence of SEQ ID NO: 3.

13. The isolated immunoglobulin heavy chain polypeptide of claim 1, which comprises the amino acid sequence of SEQ ID NO: 4.

14. The isolated immunoglobulin heavy chain polypeptide of claim 1, which comprises the amino acid sequence of SEQ ID NO: 5.

15. The isolated immunoglobulin heavy chain polypeptide of claim 1, which comprises the amino acid sequence of SEQ ID NO: 27.

16. The isolated immunoglobulin light chain polypeptide of claim 2, which comprises the amino acid sequence of SEQ ID NO: 7.

17. The isolated immunoglobulin light chain polypeptide of claim 2, which comprises the amino acid sequence of SEQ ID NO: 8.

18. The isolated immunoglobulin light chain polypeptide of claim 2, which comprises the amino acid sequence of SEQ ID NO: 9.

19. The isolated immunoglobulin light chain polypeptide of claim 2, which comprises the amino acid sequence of SEQ ID NO: 10.

20. The isolated immunoglobulin light chain polypeptide of claim 2, which comprises the amino acid sequence of SEQ ID NO: 11.

21. The isolated immunoglobulin light chain polypeptide of claim 2, which comprises the amino acid sequence of SEQ ID NO: 12.

22. The isolated immunoglobulin light chain polypeptide of claim 2, which comprises the amino acid sequence of SEQ ID NO: 13.

23. The isolated immunoglobulin light chain polypeptide of claim 2, which comprises the amino acid sequence of SEQ ID NO: 14.

24. The isolated immunoglobulin light chain polypeptide of claim 2, which comprises the amino acid sequence of SEQ ID NO: 15.

25. The isolated immunoglobulin light chain polypeptide of claim 2, which comprises the amino acid sequence of SEQ ID NO: 16.

26. The isolated immunoglobulin light chain polypeptide of claim 2, which comprises the amino acid sequence of SEQ ID NO: 17.

27. The isolated immunoglobulin light chain polypeptide of claim 2, which comprises the amino acid sequence of SEQ ID NO: 18.

28. The isolated immunoglobulin light chain polypeptide of claim 2, which comprises the amino acid sequence of SEQ ID NO: 19.

29. The isolated immunoglobulin light chain polypeptide of claim 2, which comprises the amino acid sequence of SEQ ID NO: 20.

30. The isolated immunoglobulin light chain polypeptide of claim 2, which comprises the amino acid sequence of SEQ ID NO: 21.

31. The isolated immunoglobulin light chain polypeptide of claim 2, which comprises the amino acid sequence of SEQ ID NO: 22.

32. The isolated immunoglobulin light chain polypeptide of claim 2, which comprises the amino acid sequence of SEQ ID NO: 23.

33. The isolated immunoglobulin light chain polypeptide of claim 2, which comprises the amino acid sequence of SEQ ID NO: 24.

34. The isolated C5-binding antibody or antigen binding fragment of claim 3, comprising the (a) immunoglobulin heavy chain polypeptide of SEQ ID NO: 3, and (b) the immunoglobulin light chain polypeptide of SEQ ID NO: 15.

* * * * *